(12) United States Patent
Zhao et al.

(10) Patent No.: US 8,192,743 B2
(45) Date of Patent: *Jun. 5, 2012

(54) RELEASABLE POLYMERIC CONJUGATES BASED ON ALIPHATIC BIODEGRADABLE LINKERS

(75) Inventors: Hong Zhao, Edison, NJ (US); Richard B. Greenwald, Somerset, NJ (US); Susan L. Adler, legal representative, Milwaukee, WI (US)

(73) Assignee: Enzon Pharmaceuticals, Inc., Piscataway, NJ (US)

( * ) Notice: Subject to any disclaimer, the term of this patent is extended or adjusted under 35 U.S.C. 154(b) by 495 days.

This patent is subject to a terminal disclaimer.

(21) Appl. No.: 12/180,187

(22) Filed: Jul. 25, 2008

(65) Prior Publication Data

US 2008/0305070 A1 Dec. 11, 2008

Related U.S. Application Data

(63) Continuation of application No. 11/011,818, filed on Dec. 14, 2004, now Pat. No. 7,413,738, which is a continuation-in-part of application No. 10/449,849, filed on May 30, 2003, now Pat. No. 7,087,229, and a continuation-in-part of application No. 10/218,167, filed on Aug. 13, 2002, now Pat. No. 7,122,189.

(51) Int. Cl.
*A61K 39/385* (2006.01)
*A61K 39/44* (2006.01)
*A01N 33/08* (2006.01)
*A01N 31/06* (2006.01)

(52) U.S. Cl. ............... 424/179.1; 424/181.1; 424/193.1; 424/194.1; 514/668; 514/716; 514/715

(58) Field of Classification Search ............... 424/179.1, 424/181.1, 193.1, 194.1; 514/668, 715, 716
See application file for complete search history.

(56) References Cited

U.S. PATENT DOCUMENTS

| | | | |
|---|---|---|---|
| 3,888,797 A | 6/1975 | Marumo et al. | |
| 4,179,337 A | 12/1979 | Davis et al. | |
| 5,643,575 A | 7/1997 | Martinez et al. | |
| 5,679,711 A | 10/1997 | Carrell et al. | |
| 5,919,455 A | 7/1999 | Greenwald et al. | |
| 6,113,906 A | 9/2000 | Greenwald et al. | |
| 7,087,229 B2 | 8/2006 | Zhao et al. | |
| 7,122,189 B2 | 10/2006 | Zhao et al. | |
| 7,273,845 B2 | 9/2007 | Zhao et al. | |
| 7,413,738 B2 * | 8/2008 | Zhao et al. | ............... 424/179.1 |
| 2005/0197290 A1 | 9/2005 | Zhao et al. | |
| 2007/0166276 A1 | 7/2007 | Zhao et al. | |

FOREIGN PATENT DOCUMENTS

| | | |
|---|---|---|
| DE | 4135115 A | 4/1993 |
| WO | 03/070726 | 8/2003 |
| WO | 2004/014424 | 2/2004 |
| WO | 2004/044222 | 5/2004 |
| WO | 2004/085386 | 10/2004 |
| WO | 2004/092191 | 10/2004 |

OTHER PUBLICATIONS

Zhao, H., et al., Linear and Branched Bicin Linkers for Releasable PEGylation of Macromolecules: Controlled Release in Vivo and in Vitro from Mono- and Multi-PEGylated Proteins, Bioconjugate Chemistry, vol. 17: 341-351, 2006.
Suggs, J. W., et al., Facile Hydrolysis and Formation of Amide Bonds by N-Hydroxyethylation of α-Amino Acids, Tetrahedron Letters, vol. 38(13): 2227-2230, 1997.
Pasut, G., et al. Protein, Peptide and Non-peptide Drug PEGylation for Therapeutic Application, Expert Opinion Therapeutic Patents, vol. 14(6): 859-894, 2004.
Greenwald, R. B., et al., A New Aliphatic Amino Prodrug System for the Delivery of Small Molecules and Proteins Utilizing Novel PEG Derivatives, J. Med. Chem, vol. 47: 726-734, 2004.
Extended European Search Report issued in European Patent Application No. 05854230.9 and dated Aug. 26, 2010.

* cited by examiner

*Primary Examiner* — Susan Hanley
(74) *Attorney, Agent, or Firm* — Lucas & Mercanti, LLP

(57) ABSTRACT

Activated polymeric bicine derivatives such as,

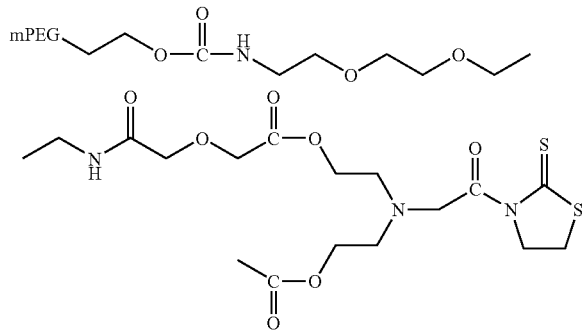

as well as conjugates made therewith are disclosed. Methods of making and using the bicine derivatives are also disclosed.

23 Claims, 5 Drawing Sheets

RELEASABLE POLYMERIC CONJUGATES BASED ON ALIPHATIC BIODEGRADABLE LINKERS

CROSS-REFERENCE TO RELATED APPLICATIONS

This patent application is a continuation of U.S. patent application Ser. No. 11/011,818 filed Dec. 14, 2004, now U.S. Pat. No. 7,413,738, which is a continuation-in-part (CIP) of U.S. patent application Ser. No. 10/449,849 filed May 30, 2003, now U.S. Pat. No. 7,087,229 and U.S. patent application Ser. No. 10/218,167 filed August 13, 2002, now U.S. Pat. No. 7,122,189, the contents of each of which are incorporated herein by reference in its entirety.

FIELD OF THE INVENTION

The present invention relates to releasable polymers which are useful in extending the in vivo circulating life of biologically active materials. The invention also relates to conjugates made with the polymers.

BACKGROUND OF THE INVENTION

Some of the initial concepts of coupling peptides or polypeptides to poly(ethylene glycol) PEG and similar water-soluble poly(alkylene oxides) are disclosed in U.S. Pat. No. 4,179,337, the disclosure of which is incorporated herein by reference. Polypeptides modified with these polymers exhibit reduced immunogenicity/antigenicity and circulate in the bloodstream longer than unmodified versions.

To conjugate poly(alkylene oxides), one of the hydroxyl end-groups is converted into a reactive functional group. This process is frequently referred to as "activation" and the product is called an "activated poly(alkylene oxide)". Other substantially non-antigenic polymers are similarly "activated" or functionalized.

The activated polymers are reacted with a therapeutic agent having nucleophilic functional groups that serve as attachment sites. One nucleophilic functional group commonly used as an attachment site is the ϵ-amino groups of lysines. Free carboxylic acid groups, suitably activated carbonyl groups, oxidized carbohydrate moieties and mercapto groups have also been used as attachment sites.

Insulin and hemoglobin were among the first therapeutic agents conjugated. These relatively large polypeptides contain several free e-amino attachment sites. A sufficient number of polymers could be attached to reduce immunogenicity and increase the circulating life without significant loss of biologic activity.

Excessive polymer conjugation and/or conjugation involving a therapeutic moiety's active site where groups associated with bioactivity are found, however, often result in loss of activity and thus therapeutic usefulness. This is often the case with lower molecular weight peptides which have few attachment sites not associated with bioactivity. Many non-peptide therapeutics also lack a sufficient number of attachment sites to obtain the benefit of polymeric modification.

One suggestion for overcoming the problems discussed above is to use longer, higher molecular weight polymers. Depending on the molecular weight desired, these materials, however, can be difficult to prepare and expensive to use. Further, they sometimes provide little improvement over more readily available polymers.

Another alternative suggested is to attach two strands of polymer via a triazine ring to amino groups of a protein. See, for example, Enzyme, 26, 49-53 (1981) and Proc. Soc. Exper. Biol. Med., 188, 364-9 (1988). Triazine, however, is a toxic substance which is difficult to reduce to acceptable levels after conjugation. In addition, triazine is a planar group and can only be double-polymer substituted. The planar structure rigidly locks the two polymer chains in place. This limits the benefits of polymer conjugation to about the same as that obtained by increasing polymer chain length. Thus, non-triazine-based activated polymers would offer substantial benefits to the art.

In the above-mentioned cases, however, the biologically active polymer conjugates were formed having substantially hydrolysis-resistant bonds (linkages) between the polymer and the parent biologically-active moiety. Thus, long-lasting conjugates which are permanently linked rather than prodrugs per se (where the parent molecule is eventually liberated in vivo) were prepared.

Commonly assigned U.S. Pat. Nos. 5,643,575, 5,919,455 and 6,113,906 disclose additional improvements relating to multiple-strands of PEG sharing a common point of attachment to a nucleophile via an aliphatic linker. Unlike the earlier triazine-based branched polymer conjugates, the aliphatic linkers allow the artisan to avoid the toxicities of triazine as well as provide other useful advantages.

In addition, over the years, several methods of preparing prodrugs have also been suggested. Prodrugs include chemical derivatives of a biologically-active parent compound which, upon administration, will eventually liberate the active parent compound in vivo. Use of prodrugs allows the artisan to modify the onset and/or duration of action of a biologically-active compound in vivo. Prodrugs are often biologically inert or substantially inactive forms of the parent or active compound. The rate of release of the active drug is influenced by several factors including the rate of hydrolysis of the linker which joins the parent biologically active compound to the prodrug carrier.

Some prodrugs based on ester or phosphate linkages have been reported. In most cases, the particular type of ester linkage used to form the prodrug provides $t_{1/2}$ for hydrolysis of up to several days in aqueous environments. Although one would expect a prodrug to have been formed, most of the conjugate is eliminated prior to sufficient hydrolysis being achieved in vivo. It would therefore be preferable to provide prodrugs which have a linkage which allows more rapid hydrolysis of the polymer-drug linkage in vivo so as to generate the parent drug compound more rapidly.

Prodrugs based on amide or carbamate linkages have also been reported. In general, amide bonds are known to be highly resistant to hydrolysis. However, it has recently been found that the C-terminal amides of e-amino acids are readily hydrolyzed at 25° C. and pH 7.4 when the N-terminus is N-hydroxyethylated with one or two hydroxyethyl groups. Bis N-2-hydroxyethyl glycine (bicine) type molecules are key to such hydrolysis reactions. Such bicine type groups have recently been employed in the synthesis of prodrugs, see commonly assigned U.S. patent application Ser. Nos. 10/218,167 and 10/449,849.

There is still room for improvement in the area of prodrug design. The present invention provides such an improvement.

SUMMARY OF THE INVENTION

In one aspect of the invention, compounds of Formula (I) are provided:

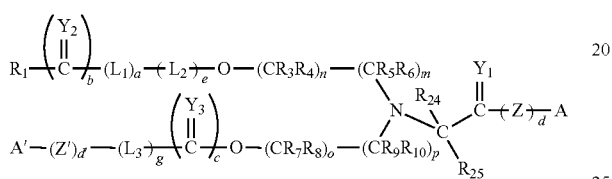

(I)

wherein:

$R^1$ is selected from the group consisting of substantially non-antigenic polymer residues, $C_{1-6}$ alkyls, $C_{2-6}$ alkenyl, $C_{2-6}$ alkynyl, aralkyls, and terminal branching groups;

Z and Z' are the same or different and are independently selected from among moieties actively transported into a target cell, hydrophobic moieties, bifunctional linking moieties and combinations thereof;

$Y_{1-3}$ may be the same or different and are selected from among O, S or $NR_{11}$;

$L_1$ and $L_3$ are independently bifunctional linkers;

$R_3 R_{11}$, $R_{24}$ and $R_{25}$ may be the same or different and are selected from the group consisting of hydrogen, $C_{1-6}$ alkyls, $C_{2-6}$ alkenyl, $C_{2-6}$ alkynyl, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$L_2$ is selected from:

—C(O)(CR$_{30}$R$_{31}$)Y$_{15}$(CR$_{32}$R$_{33}$)C(O)NR$_{35}$— or

—C(O)(CR$_{30}$R$_{31}$)(CR$_{32}$R$_{33}$)C(O)NR$_{35}$— wherein:

$Y_{15}$ is selected from O, S, $NR_{34}$ or $CHt_2$, and $R_{30-35}$ may be the same or different and are selected from H, alkyl, alkenyl, alkynyl, heteroalkyl or aryl;

A and A' may be the same or different and are independently selected from among alkyl groups, leaving groups, functional groups, diagnostic agents, targeting moieties, biologically active moieties and OH;

a, g, e, may be the same or different and are independently 0 or a positive integer from about 1 to about 5, preferably 0 or 1;

b, c, d and d' may be the same or different and are independently 0 or 1, and m, n, o, and p may be the same or different and are independently a positive integer from about 1 to about 6, provided that (a+e) is equal to or greater than 1.

Another aspect of the invention includes bifunctional compounds that are formed when $R_1$ is a polymeric residue which includes both an alpha and omega terminal linking group. In this aspect of the invention, the artisan is capable of attaching two equivalents of a biologically active agent drug, protein, polypeptide, oligonucleotide, diagnostic agent etc. to the polymeric (preferably PEG) bicine system. An example of such a bifunctional polymer conjugate is illustrated below as formula (II):

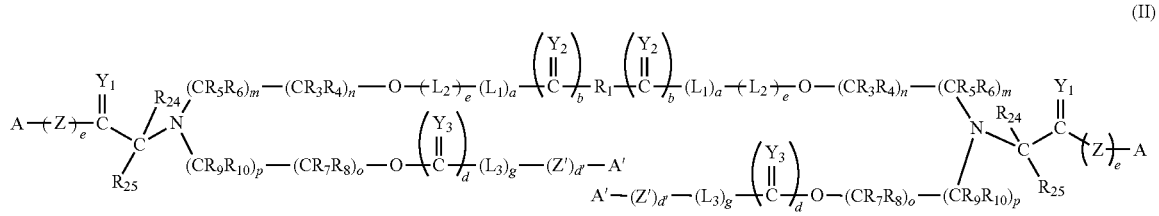

(II)

wherein,

Z and Z' are independently bifunctional linking groups or

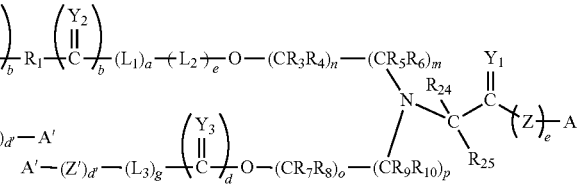

wherein, $Y_4$ is O, S or $NR_{11}$ and $L_5$ is a bifunctional linker, and all other variables are as described above.

Methods of preparing the compounds of the present invention and methods of treatment using the same are also provided.

For purposes of the present invention, the term "residue" shall be understood to mean that portion of a compound, to which it refers, that remains after it has undergone a substitution reaction in which the polymeric prodrug carrier portion has been attached.

For purposes of the present invention, the term "polymeric residue" or "PEG residue" shall each be understood to mean that portion of the polymer or PEG which remains after it has undergone a reaction with a biologically active compound.

For purposes of the present invention, the term "alkyl" shall be understood to include straight, branched, substituted, e.g. halo-, alkoxy-, nitro-, $C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkyjiylaminos, hydroxyalkynyls and mercaptoallynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

The term "sufficient amounts" for purposes of the present invention shall mean an amount which achieves a therapeutic effect as such effect is understood by those of ordinary skill in the art.

For purposes of the present invention, "effectively non-antigenic" and "substantially non-antigenic" shall be understood to include all polymeric materials understood in the art as being substantially nontoxic and not eliciting an appreciable immune response in mammals.

For purposes of the present invention, a "positive integer" shall be understood to mean a positive whole number, preferably from about 1 to 6 and more preferably 1 or 2.

One chief advantage of the present invention is that the bicine linker allows for the manipulation of the hydrolysis rate of the prodrug, thereby releasing the native entities at various rates in vivo as well as in vitro. For example, various bifunctional moieties, including amino acid or short peptide residues can be included as part of any of $L_{1-3}$ to modulate the rate of hydrolysis of the prodrug and/or cellular uptake, etc. is vivo and in vitro.

Another advantage of this invention is that by attaching the polymer moiety to only one arm of the bicine system, the conjugation process is cleaner and faster.

A further advantage of this invention is that the metabolic profile is improved due to little or no formation of impurities or by-products during hydrolysis. This lack of impurity formation also leads to easier purification.

Still another advantage of this invention is that one has the ability to attach both a targeting moiety as well as a biologically active moiety i.e. a drug, to the same polymer platform thereby increasing the potential of having enhanced therapeutic efficacy.

Another advantage of the invention is that the target compounds delivered via this novel polymeric transport system often demonstrate a measurable increase in aqueous solubility and circulating life in vivo especially in the case of small molecules.

DETAILED DESCRIPTION OF THE INVENTION

A. Formula (I)

Figure 1:
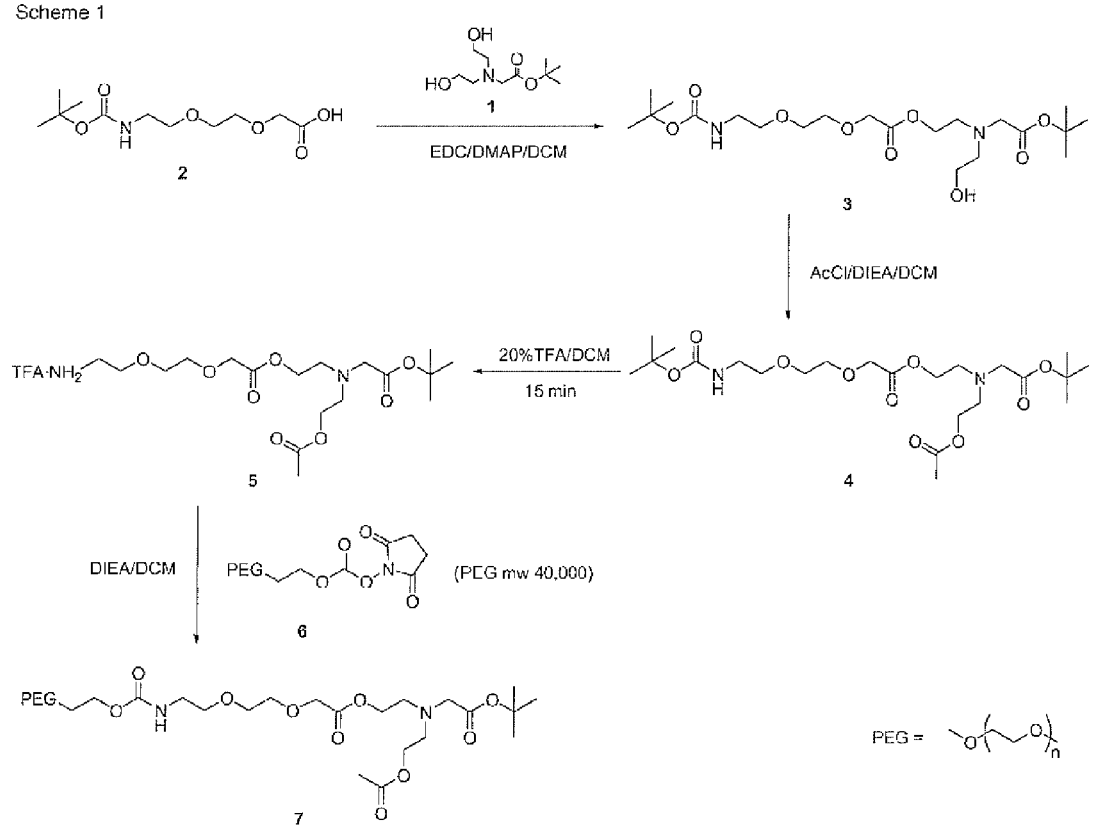
FIG. 1 provides reaction schemes corresponding to Examples 1-3.
Figure 2:
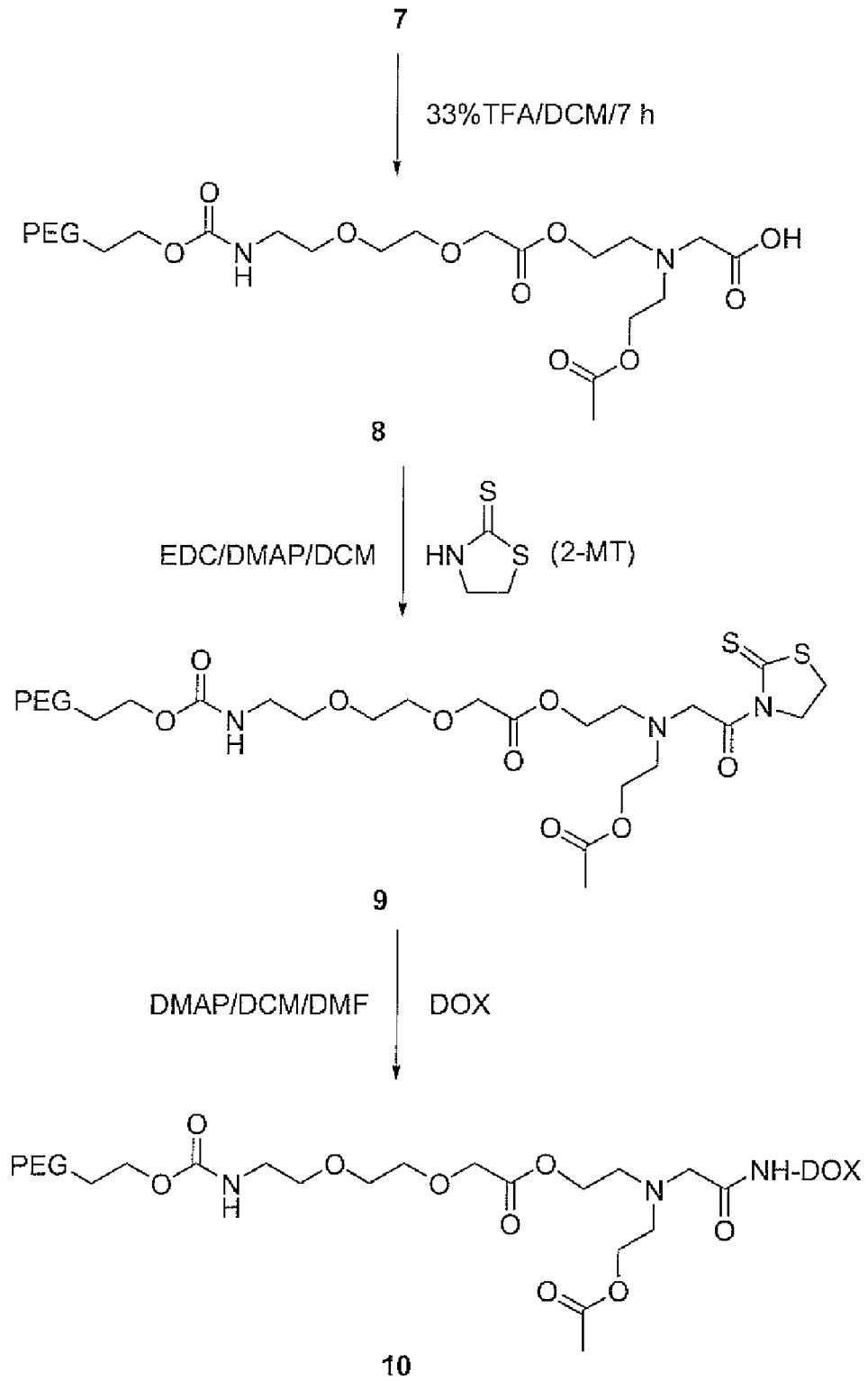
FIG. 2 provides reaction schemes corresponding to Examples 4-6.
Figure 3:
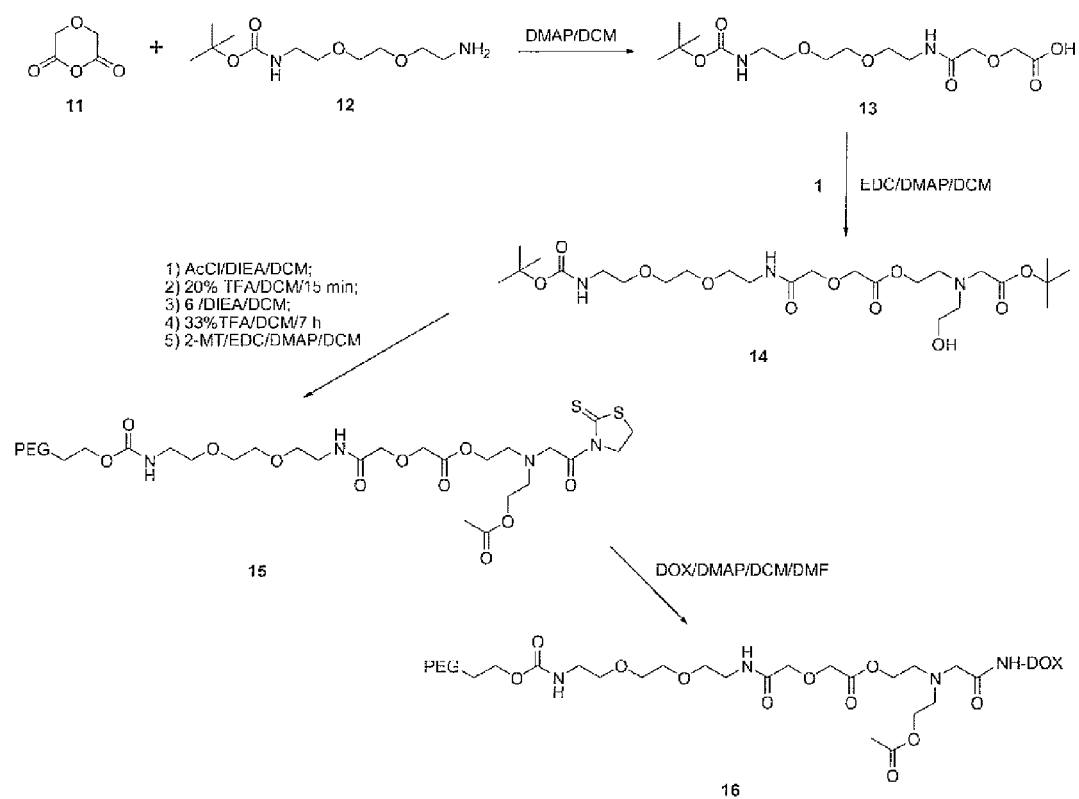
FIG. 3 provides reaction schemes corresponding to Examples 7-10.
Figure 4:
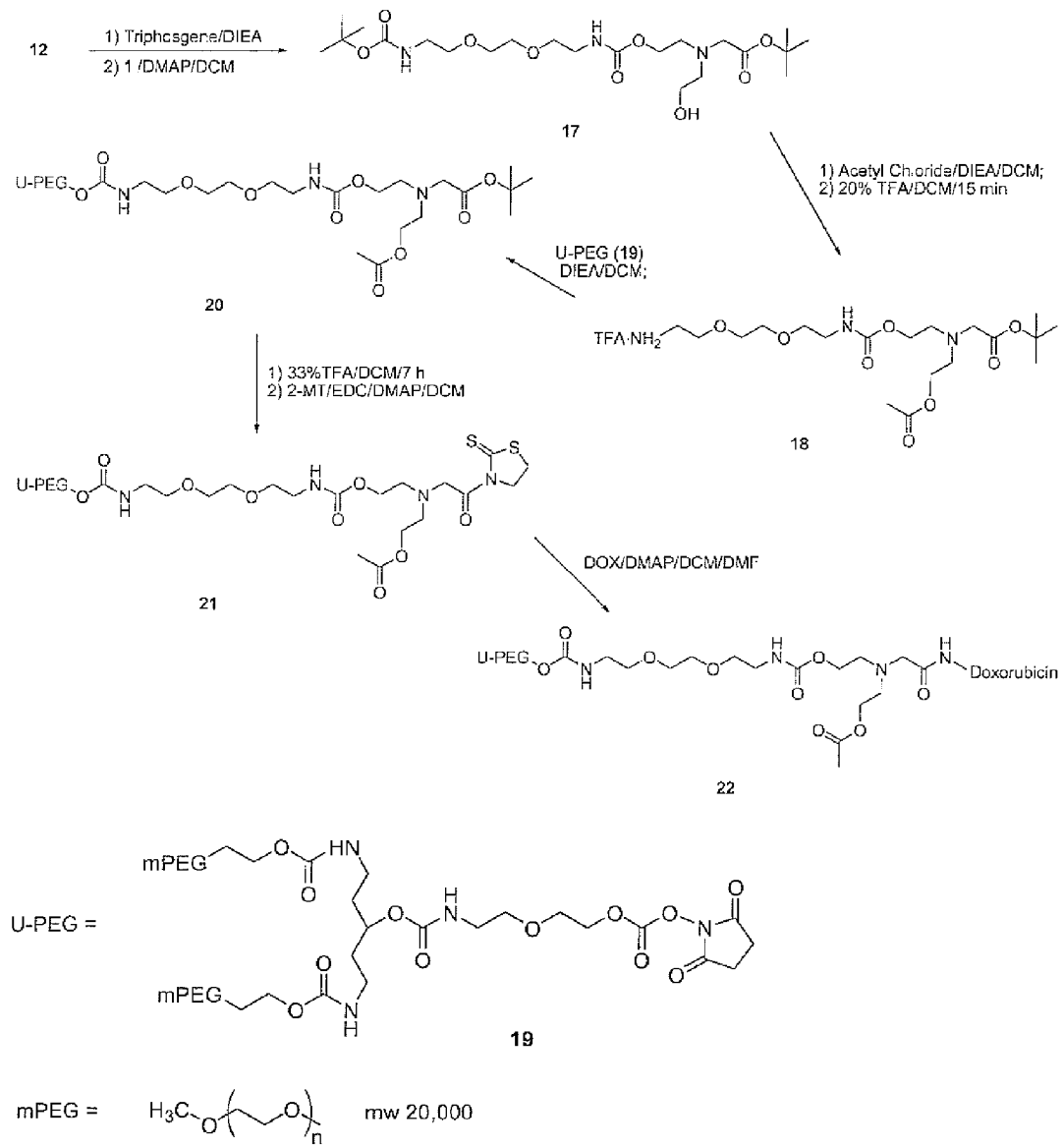
FIG. 4 provides reaction schemes corresponding to Examples 11-15.
Figure 5:
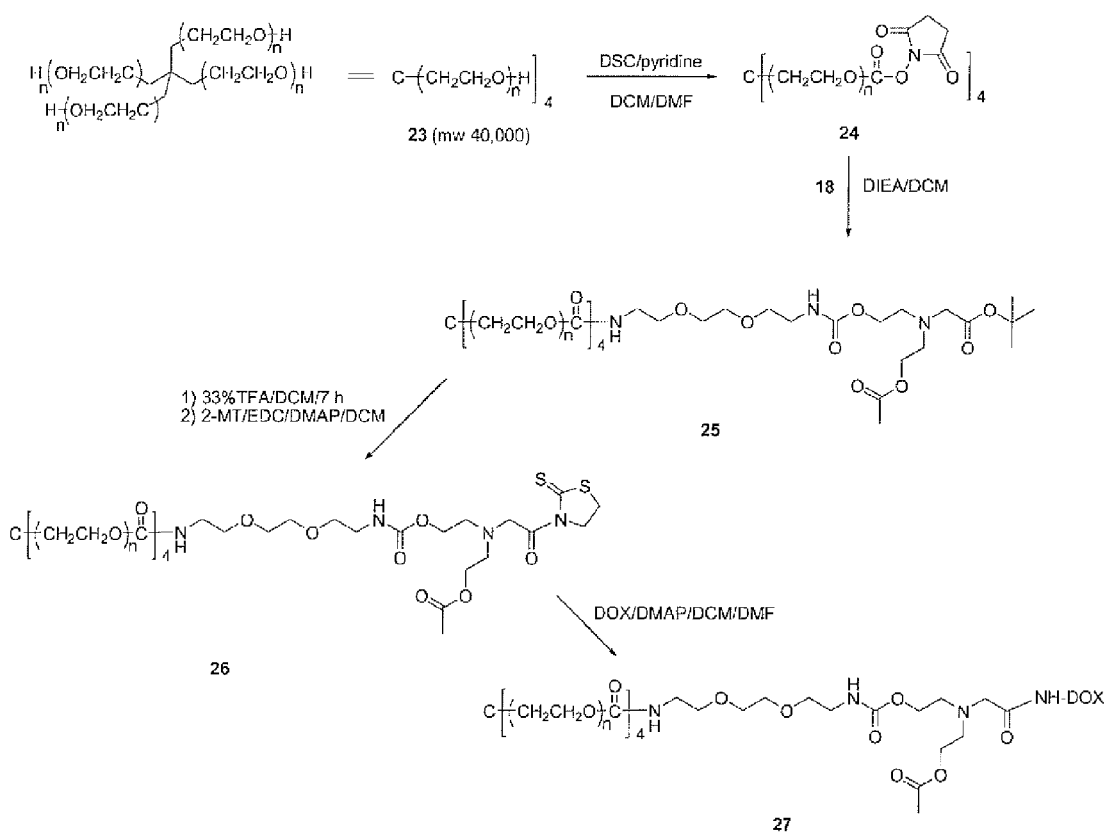
FIG. 5 provides reaction schemes corresponding to Examples 16-19.

In one embodiment of the invention, there are provided compounds of formula (I):

(I)

$$R_1-\left(\overset{Y_2}{\underset{\|}{C}}\right)_b-(L_1)_a-(L_2)_e-O-(CR_3R_4)_n-(CR_5R_6)_m-\overset{R_{24}}{\underset{N}{\diagdown}}\overset{Y_1}{\underset{\|}{C}}-(Z)_d-A$$
$$A'-(Z')_d-(L_3)_g-\left(\overset{Y_3}{\underset{\|}{C}}\right)_c-O-(CR_7R_8)_o-(CR_9R_{10})_p-\overset{\diagup}{\underset{R_{25}}{}}$$

wherein:
$R_1$ is selected from the group consisting of substantially non-antigenic polymer residues, $C_{1-6}$ alkyls, $C_{2-6}$ alkenyl, $C_{2-6}$ alkynyl, aralkyls, and terminal branching groups;

Z and Z' are the same or different and are independently selected from among moieties actively transported into a target cell, hydrophobic moieties, bifunctional linking moieties and combinations thereof;

$Y_{1-3}$ may be the same or different and are selected from among O, S or $NR_{11}$;

$L_1$ and $L_3$ are independently bifunctional linkers;

$R_3$-$R_{11}$, $R_{24}$ and $R_{25}$ may be the same or different and are selected from the group consisting of hydrogen, $C_{1-6}$ alkyls, $C_{2-6}$ alkenyl, $C_{2-6}$ alkynyl, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, alkyls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$L_2$ is selected from:

—C(O)(CR$_{30}$R$_{31}$)Y$_{15}$(CR$_{32}$R$_{33}$)C(O)NR$_{35}$— or

—C(O)(C$_{30}$R$_{31}$)(CR$_{32}$R$_{33}$)C(O)NR$_{35}$— wherein:
$Y_{15}$ is selected from O, S, $NR_{34}$ or $CH_2$, and
$R_{30-35}$ may be the same or different and are selected from H, alkyl, alkenyl, alkynyl, heteroalkyl or aryl;

A and A' are the same or different and are independently selected from among alkyl groups, leaving groups, functional groups, diagnostic agents, targeting moieties, biologically active moieties and OH;

a, g, e, may be the same or different and are independently 0 or a positive integer from about 1 to about 5, preferably 0 or 1;

b, c, d and d' are independently 0 or 1, and m, n, o, and p are independently positive integers, provided that (a+e) is equal to or greater than 1.

In certain preferred aspects of the invention, $R_1$ includes a substantially non-antigenic polymeric residue such as a polyethylene glycol (PEG) group. Optionally, $R_1$ includes a capping group designated herein as J. Preferred J groups used for polymer capping include moieties such as OH, $NH_2$, SH, $CO_2H$, $C_{1-6}$ alkyl moieties, such as $CH_3$, and compounds of formula (III):

(III)

$$A-(Z)_d-\overset{Y_1}{\underset{\|}{C}}\overset{R_{24}}{\underset{\diagdown}{\diagup}}\overset{(CR_5R_6)_m-(CR_3R_4)_n-O-(L_2)_e-(L_1)_a-\left(\overset{Y_2}{\underset{\|}{C}}\right)_b-}{\underset{(CR_9R_{10})_p-(CR_7R_8)_o-O-\left(\overset{Y_3}{\underset{\|}{C}}\right)_c-(L_3)_g-(Z')_{d'}-A'}{}}$$

where all variables are as previously defined.

With regard to the other variables which comprise the formulae of the present invention, the following are preferred in certain aspects of the invention:

in certain aspects, $R_1$ is a polyalkylene oxide residue, and more preferably polyethylene glycol residue;

in other aspects, $R_1$ is a bicine-based terminal branching group described in more detail below to allow multiple polymer strand loading;

in another aspect, $R_1$ is preferably a functional group or biologically active moiety, and A' is a functional group, targeting moiety or diagnostic agent;

$R_3$-$R_{11}$, and $R_{24-25}$ are each hydrogen, and a, b, c, e, m, n, o and p are each preferably 1.

Preferably, Z and Z' are

as defined above, or, alternatively comprise an amino acid residue, a peptide residue, a group which is actively transported into a target cell, hydrophobic or has combinations of such properties, such that when combined with biologically active A groups, prodrugs are formed which release from the bicine polymeric portion of formulae (I) and (II). See also commonly assigned U.S. Ser. No. 09/758,993, the contents of which are incorporated herein by reference.

B. Substantially Non-Antigenic Polymers

As stated above, $R_1$ is preferably a water soluble polymer residue which is preferably, substantially non-antigenic, such as, polyalkylene oxide (PAO) and more preferably polyethylene glycol such as MPEG. For purposes of illustration and not limitation, the polyethylene glycol (PEG) residue portion of $R_1$, can be selected from among:

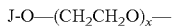

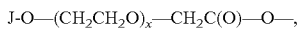

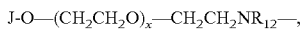

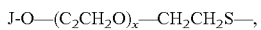

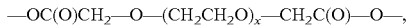

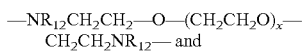

wherein:

x is the degree of polymerization;

$R_{12}$ is selected from among hydrogen, $C_{1-6}$ alkyls, $C_{2-6}$ alkenyls, $C_{2-6}$ alkynyls, $C_{3-12}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenyloxy and $C_{1-6}$ heteroalkoxy, and J is a capping group as described above with regard to Formula II.

In one particularly preferred embodiment, $R_1$ is selected from among

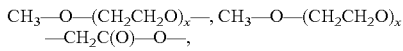

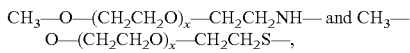

where x is a positive integer, preferably selected so that the weight average molecular weight from about 2,000 to about 40,000 Da. In alternative aspects of the invention, the molecular weight of the polymer ranges from several hundred up to 40,000 or greater, depending upon the needs of the artisan.

Also contemplated within the scope of the invention, $R_1$ is selected from among the branched polymer residues described in commonly assigned U.S. Pat. Nos. 5,605,976, 5,643,575, 5,919,455 and 6,113,906 the disclosure of each being incorporated herein by reference. Among these general formulae, the following are preferred:

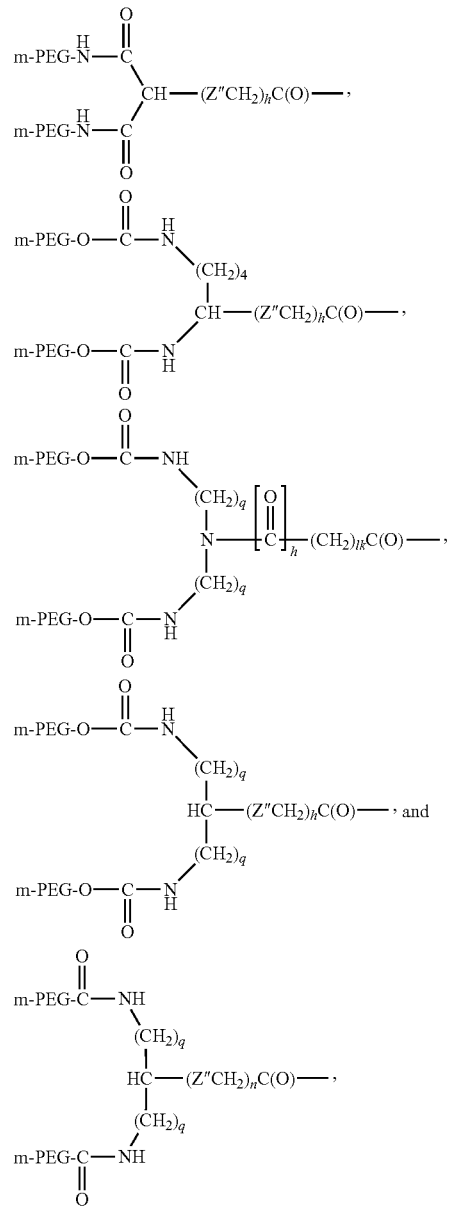

wherein:

(q) is an integer of from about 1 to about 5;

Z" is O, $NR_{13}$, S, SO or $SO_2$; where $R_{13}$ is H, $C_{1-8}$ alkyl, $C_{1-8}$ branched alkyl, $C_{1-8}$ substituted allyl, aryl or aralkyl;

(h) is 0 or 1;

(k) is a positive integer, preferably from about 1 to about 6.

Other branched activated polymers which are contemplated within the scope of this invention are preferably selected from among those compounds described in commonly assigned PCT publication numbers WO02/065988 and WO02/066066, the disclosure of each being incorporated herein by reference. Within these general formulae, the following are preferred:

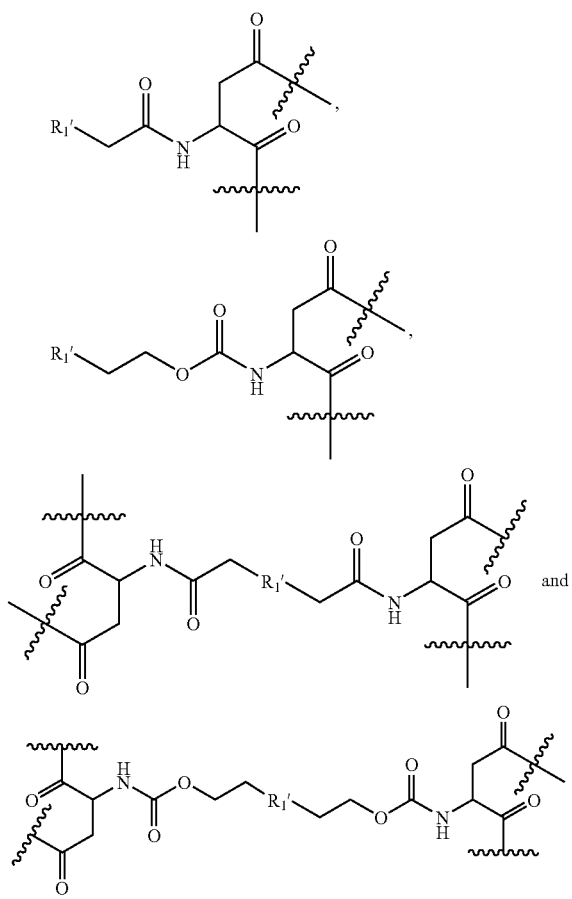

wherein:
R$_{1'}$ is a polymeric residue such as PEG.

In yet another preferred embodiment, R$_1$ is a polymeric residue of the formula:

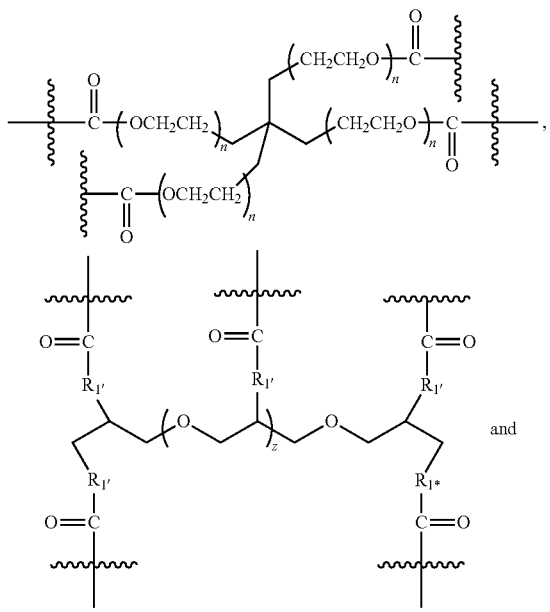

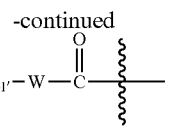

wherein:
R$_{1'}$ is a polymeric residue such as PEG;
W is a bifunctional linker, such as O, amino acid,

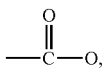

—(CH$_2$)$_y$—, and —NH(CH$_2$CH$_2$O)$_2$—;
z is 0, 1, 2, 3 or 4;
n is a positive integer, preferably from about 1 to about 500, more preferably about 200, and
y is a positive integer, preferably from about 1 to about 6.
PEG is generally represented by the structure:

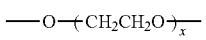

and R$_{1'}$ preferably comprises a residue of this formula.

The degree of polymerization for the polymer (x) can be from about 10 to about 2,300. This represents the number of repeating units in the polymer chain and is dependent on the molecular weight of the polymer. Preferably, x is a positive integer; selected so that the weight average molecular weight is from about 2,000 to about 40,000 Da. The (J) moiety is a capping group as defined herein, i.e. a group which is found on the terminal of the polymer and, in some aspects, can be selected from any of NH$_2$, OH, SH, CO$_2$H, C$_{1-6}$ alkyls or other PEG terminal activating groups, as such groups are understood by those of ordinary skill.

Also useful are polypropylene glycols, branched PEG derivatives such as those described in commonly-assigned U.S. Pat. No. 5,643,575 (the '575 patent), "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. The branching afforded by the '575 patent allows secondary or tertiary branching from the bicine group as a way of increasing polymer loading on a biologically active molecule or enzyme from a single point of attachment. It will be understood that the water-soluble polymer can be functionalized for attachment to the bifunctional linkage groups if required without undue experimentation.

Although PAO's and PEG's can vary substantially in weight average molecular weight, preferably, R$_1$ and R$_{1'}$ can have a weight average molecular weight of from about 2,000 to about 40,000 Da in most aspects of the invention.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, R$_1$ and R$_{1'}$, are optionally selected from among one or more effectively non-antigenic materials such as dextran, polyvinyl alcohols, carbohydrate-based polymers, hydroxypropylmeth-acrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated and that other polyalkylene oxide derivatives such as the polypropylene glycols, etc. are also contemplated.

The polymers of the present invention can also be copolymerized with bifunctional materials such as poly(alkylene glycol) diamines to form interpenetrating polymer networks suitable for use in permeable contact lenses, wound dressings, drug delivery devices and the like. The steric limitations and water solubility of such branching will be readily recognized by one of ordinary skill in the alt. Preferably, however, the molecular weight of multiple branched polymers should not exceed 80,000 daltons.

C. Bifunctional Linker Groups: $L_1$, $L_2$, $L_3$ and $L_5$

In many aspects of the invention, and formula (I) in particular, $L_1$ and $L_3$ are linking groups which facilitate attachment of the bicine derivative to the polymer strands or other moieties, e.g. $R_1$ and $A'$. The linkage provided can be either direct or through further coupling groups known to those of ordinary skill. Other L groups are mentioned in the specification and they are understood to be selected from among the same groups as $L_1$. While $L_2$ and $L_5$ are further defined below, in one aspect of the invention, $L_1$ and $L_3$ are independently selected from among:

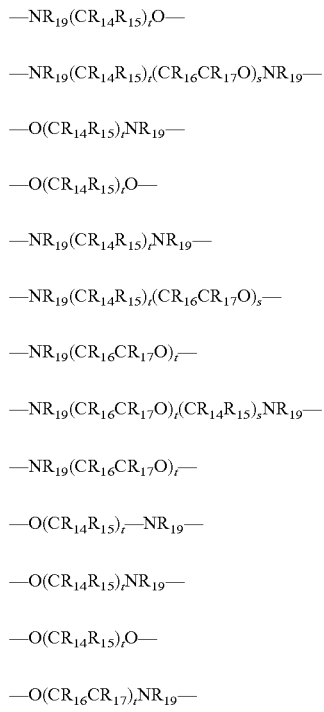

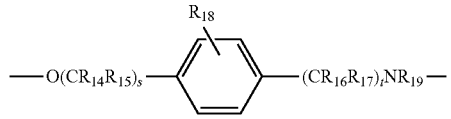

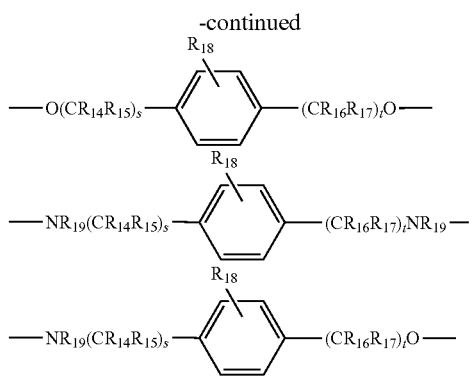

wherein:

$R_{14}$-$R_{17}$ and $R_{19}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and $R_{18}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and t and s are individually selected positive integers, preferably from about 1 to about 4.

In other aspects of the invention, $L_1$ and $L_3$ can include amino acid residues. The amino acid can be selected from any of the known naturally-occurring L-amino acids is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. When $L_1$ includes a peptide, the peptide ranges in size, for instance, from about 2 to about 10 amino acid residues. In one preferred embodiment, the peptide is Gly-Phe-Leu-Gly.

The amino acid residues are preferably of the formula

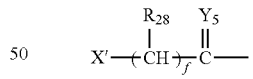

wherein X' is O, S or $NR_{26}$, $Y_5$ is O, S or $NR_{27}$, and $R_{26}$, $R_{27}$ and $R_{28}$ are independently selected from the same group as that which defines $R_3$ but each is preferably H or lower alkyl (i.e. $C_{1-6}$ alkyl); and f is a positive integer from about 1 to about 10, preferably 1.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-amino-adipic acid, beta-alanine, beta-aminopropionic acid, 2-aminobutyric acid, 4-amino-butyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, n-ethyl-glycine, N-ethylasparagine, 3-hydroxyproline, 4-hydroxyproline, isodemosine, allo-isoleucine, N-methylglycine, sarcosine, N-methylisoleucine, 6-N-methyl-lysine, N-methylvaline, norvaline, norleucine, ornithine, and others too numerous to mention, that are listed in 63 Fed. Reg., 29620, 29622, incorporated by reference herein.

Short peptides are, for example, peptides ranging from 2 to about 10, or more, amino acid residues, as mentioned supra.

More preferably, $L_1$ and $L_3$ are independently selected from:

—NH(CH$_2$CH$_2$)$_2$O—

—NH(CH$_2$CH$_2$)(CH$_2$CH$_2$O)NH—

—O(CH$_2$CH$_2$)NH—

—O(CH$_2$CH$_2$)O—

—NH(CH$_2$CH$_2$)NH—

—NH(CH$_2$CH$_2$)(CH$_2$CH$_2$O)—

—NH(CH$_2$CH$_2$O)—

—NH(CH$_2$CH$_2$O)(CH$_2$)NH—

—NH(CH$_2$CH$_2$O)$_2$—

—O(CH$_2$)$_3$NH—

—O(CH$_2$)$_3$O—

—O(CH$_2$CH$_2$O)$_2$NH—

In another embodiment of the invention, $L_2$ is selected from:

—C(O)CR$_{30}$R$_{30}$OCR$_{32}$R$_{33}$C(O)NR$_{35}$—;

—C(O)CR$_{30}$R$_{31}$NR$_{34}$CR$_{32}$R$_{33}$C(O)NR$_{35}$—;

—C(O)CR$_{30}$R$_{31}$SCR$_{32}$R$_{33}$C(O)NR$_{35}$—, or

—C(O)(CR$_{30}$R$_{31}$)$_n$C(O)NR$_{35}$—;

wherein:
$R_{30-35}$ are independently selected from H, $C_{1-6}$ alkyl, $C_{2-6}$ alkenyl, $C_{2-6}$ alkynyl, $C_{1-6}$ heteroalkyl or aryl, and
n is a positive integer preferably from about 1 to about 3.
Preferably, $L_2$ is selected from:

—C(O)CH$_2$OCH$_2$C(O)NH—;

—C(O)CH$_2$NHCH$_2$C(O)NH—;

—C(O)CH$_2$SCH$_2$C(O)NH—;

—C(O)CH$_2$CH$_2$CH$_2$C(O)NH—, or

—C(O)CH$_2$CH$_2$C(O)NH—

A chief advantage of the invention is that the artisan can control the rate of hydrolysis or release of the biologically active moiety or drug from the polymeric bicine platform. Depending on the specific linkers selected, one of ordinary skill can modify the compounds to manipulate the rate of hydrolysis. This preferred aspect of the invention allows the artisan to regulate the rate at which the biologically active moiety is delivered to the intended target. In situations where it would be desirable to have a quick release of the biologically active moiety or drug, incorporation of the $L_2$ linker provides for an enhanced rate of hydrolysis. In contrast, to the earlier bicine based polymer platforms disclosed in commonly assigned U.S. patent application Ser. No. 10/218,167 wherein the release of the moiety or drug from the platform often depends on conditions such as pH or the presence of enzymes, the linker $L_2$ by virtue of anchimeric assistance, is able to substantially enhance the rate of at which the biologically active moiety or drug is released from the polymeric platform independent of the pH conditions or the presence or absence of enzymes. In the presence of enzymes, however, the rate of hydrolysis will be controlled by either the anchimeric assistance when applicable or by the enzymatic reactions whichever is faster. Accordingly, the rate of hydrolysis is highly dependent on the type of linkers used between the bicine moiety itself and the PEG portion.

D. Z and Z' Moieties and their Function

In one aspect of the invention Z and Z' are $L_5$-C($=$Y$_4$) wherein $L_5$ is a bifunctional linker and is selected from among the same groups as $L_1$ and $Y_4$ is selected from among the same groups as that which defines $Y_{1-3}$. In this aspect of the invention, the Z and 7' groups serve as linkages between the A groups and the remainder of the bicine transport form.

In other aspects of the invention, Z and Z' are moieties that are actively transported into a target cell, hydrophobic moieties, and combinations thereof. Although Z and Z' are preferably monovalent, they can optionally be bivalent or multivalent so to allow attachment of more than one A group to the bicine-based polymer. In order to achieve the active transport, Z and Z' can include an amino acid, peptide residue, or polyamine residue, such as any of those described above with regard to $L_1$, a sugar residue, a fatty acid residue, a $C_{6-18}$ alkyl, a substituted aryl, a heteroaryl, —C($=$O), —C($=$S) or —C(—NR$_{29}$), wherein $R_{29}$ is H, lower alkyl, etc.

This aspect of the invention is broadly based upon the principle that biologically active materials suitable for incorporation into the bicine-polymer-based prodrug conjugates may themselves be substances/compounds which are not active after hydrolytic release from the bicine-linked composition, but which will become active after undergoing a further chemical process/reaction. With this embodiment, a therapeutic or diagnostic agent, peptide, polypeptide, etc. that is delivered to the bloodstream by the bicine-based polymer system, will remain inactive until entering or being actively transported into a target cell of interest, whereupon it is activated by intracellular chemistry, e.g., by an enzyme or enzyme system present in that tissue or cell.

The prodrugs of this aspect of the invention are prepared so that in vivo hydrolysis of the bicine-polymer-based conjugate cleaves the conjugate so as to release the active biological material (designated A herein) into extracellular fluid, while still linked to the Z or Z' moiety. The biologically active materials in this aspect of the invention are preferably, but not exclusively, small molecule therapeutic and/or diagnostic agents. For example, one potential Z-A combination is leucine-doxorubicin, another is amino acid-linked camptothecin or paclitaxel and the tissue to be treated is tumor tissue.

Without intending to be bound by any theory or hypothesis as to how the invention might operate, it is believed that, depending upon the additional moiety selected as a transport enhancer, the rate of transport of a biologically active material into tumor cells is by the delivery of a biologically active material into extracellular tissue space, e.g., of a tissue exhibiting an EPR effect, in a protected and/or transport-enhanced form.

In a further still option, the transport enhancer (Z or Z') is selected from among known substrates for a cell membrane transport system. Simply by way of example, cells are known to actively transport certain nutrients and endocrine factors, and the like, and such nutrients, or analogs thereof are readily employed to enhance active transport of a biologically effective material into target cells. Examples of these nutrients include amino acid residues, peptides, e.g., short peptides ranging in size from about 2 to about 10 residues or more, simple sugars and fatty acids, endocrine factors, and the like.

Short peptides are, for example, peptides ranging from 2 to about 10, or more, amino acid residues, as mentioned supra. In this embodiment of the invention, it is believed that such peptide transport enhancers need not be hydrophobic, but are thought to function in other ways to enhance uptake and/or to protect the linked small molecule agents from premature hydrolysis in the general bloodstream. For instance, peptide transport enhancers, such as, for example polyarginine, and other transport enhancers of similar molecular weight ranges, are thought to sterically hinder cleavage from the biologically active agent by plasma-based hydrolytic enzymes, but are then cleaved within a target cell by various peptides and/or proteases, such as cathepsins.

In certain preferred aspects Z and Z' are hydrophobic moieties. Without meaning to be bound to any theory or hypothesis as to how hydrophobicity contributes to efficacy, it is believed that a hydrophobic moiety inhibits the extracellular cleavage of the transport enhancer away from the active biological agent, by inhibiting the attack of hydrolytic enzymes, etc. present in the extracellular tissue space, e.g., in the plasma. Thus, some preferred transport enhancers include, e.g., hydrophobic amino acids such as alanine, valine, leucine, isoleucine, methionine, proline, phenylalanine, tyrosine, and tryptophane, as well as non-naturally occurring derivatives, such as, γ-amino acid, and analogs thereof, as mentioned supra.

In a further option, the transport enhancer is a hydrophobic organic moiety. Simply by way of example, the organic moiety is a $C_{6-18}$, or larger, alkyl, aryl or heteroaryl-substituted or nonsubstituted. The organic moiety transport enhancer is also contemplated to encompass and include organic functional groups including, e.g., —C(=S) and/or —C(=O), E. Formula (I) A, A' and D Groups 1. Leaving or Activating Groups In those aspects where A and A' are leaving or activating groups, suitable moieties include, without limitation, groups such as N-hydroxybenzotriazolyl, halogen, N-hydroxyphthalimidyl, p-nitrophenoxyl, imidazolyl, N-hydroxysuccinimidyl; thiazolidinyl thione, O-acyl ureas, pentafluorophenoxyl, 2,4,6-trichlorophenoxyl or other suitable leaving groups that will be apparent to those of ordinary skill.

For purposes of the present invention, leaving groups are to be understood as those groups which are capable of reacting with a nucleophile found on the desired target, i.e. a biologically active moiety, a diagnostic agent, a targeting moiety, a bifunctional spacer, intermediate, etc. The targets thus contain a group for displacement, such as $NH_2$ groups found on proteins, peptides, enzymes, naturally or chemically synthesized therapeutic molecules such as doxorubicin, spacers such as mono-protected diamines.

The compounds of the present invention can also include a spacer group between the bicine group and the leaving group or attached target (drug) if desired. The spacer moiety may be a heteroalkyl, alkoxy, alkyl containing up to 18 carbon atoms or even an additional polymer chain. The spacer moieties can added using standard synthesis techniques. It is to be understood that those moieties selected for A and A' can also react with other moieties besides biologically active nucleophiles.

2. Functional Groups

A and A' can also be functional groups. Non-limiting examples of such functional groups include maleimidyl, vinyl, residues of sulfone, hydroxy, amino, carboxy, mercapto, hydrazide, carbazate and the like which can be attached to the bicine portion through an amine-containing spacer. Once attached to the bicine portion, the functional group, (e.g. maleimide), can be used to attach the bicine-polymer to a target such as the cysteine residue of a polypeptide, amino acid or peptide spacer, etc.

3. Biologically Active Moieties

In those aspects of formula (I) where A and A' are residues of an amine- or hydroxyl-containing compound. A non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, melphalan, Ara-C (cytosine arabinoside) and related anti-metabolite compounds, e.g., gemcitabine, etc. Alternatively, the moiety can be a residue of an amine- or hydroxyl-containing cardiovascular agent, anti-neoplastic agent such as camptothecin and paclitaxel, anti-infective, anti-fungal such as nystatin, fluconazole and amphotericin B, anti-anxiety agent, gastrointestinal agent, central nervous system-activating agent, analgesic, fertility agent, contraceptive agent, anti-inflammatory agent, steroidal agent, agent, etc.

In addition to the foregoing, the biologically active moiety can also be a residue of an enzyme, protein, polypeptide, monoclonal antibodies, immunoconjugates, such as, SS1P, single to chain antigen binding proteins (SCA's), such as, CC49, and fragments thereof are also contemplated. Suitable proteins include but are not limited to, polypeptides, enzymes, peptides and the like having at least one available group for polymer attachment, e.g. an e-amino, cystinylthio, N-terminal amino, including materials which have physiological or pharmacological activities as well as those which are able to catalyze reactions in organic solvents.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, etc., alpha, β and γ interferons, colony stimulating factors including granulocyte colony stimulating factors, platelet derived growth factors and phospholipase-activating protein (PLAP) as well as Thymosin alpha 1 and Secretin. Other proteins of general biological or therapeutic interest include insulin, plant proteins such as lectins and ricins, tumor necrosis factors and related proteins, growth factors such as transforming growth factors, such as TGF alpha or TGF β and epidermal growth factors, hormones, somatomedins, erythropoietin, pigmentary hormones, hypothalamic releasing factors, antidiuretic hormones, prolactin, chloronic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubiin oxidase. Carbohydrate-specific enzymes of interest include glucose oxidases, glucodases, galactosidases, glucocerebrosidases, glucoturonidases, etc.

Also included herein is any portion of a biological polymer demonstrating in vivo bioactivity. This includes amino acid sequences, nucleic acids (DNA, RNA), peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino- or hydroxyl-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds/compositions can be similarly modified without undue experimentation. It is to be understood that those biologically active materials not specifically mentioned but having suitable attachment groups are also intended and are within the scope of the present invention.

The only limitations on the types of amino- or hydroxyl containing molecules suitable for inclusion herein is that there is available at least one (primary or secondary) amine- or hydroxyl-which can react and link with the polymeric conjugate and that there is not substantial loss of bioactivity after the prodrug system releases and regenerates the parent compound.

4. Alkyl Groups

In those aspects of formula (I) where A and A' are alkyl groups, a non-limiting list of suitable groups consists of $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aralkyls, $C_{1-6}$ heteroalkyls, and substituted $C_{1-6}$ heteroalkyls.

5. Diagnostic Agents

In those aspects of formula (I) where A and A' are diagnostic agents, a non-limiting list of suitable agents includes dyes, chelating agents, and isotope labeled compounds and other labeling compounds such as Green Fluorescent Protein (GFP).

6. Targeting Moieties

In those aspects of formula (I) where A and A' are targeting moieties, a non-limiting list of suitable agents includes, peptides such as, TAT peptide and U-7 peptide, single chain antibodies such as, CC49, and small molecules, such as, for example, taurine and biotin.

F. Synthesis of Bicine Linked Polymers

Synthesis of specific bicine-based polymer compounds is set forth in the Examples. Turning now to FIG. 1 for the purpose of illustration, one preferred method includes:

1) reacting about one equivalent of an extended blocked bifunctional linker such as:

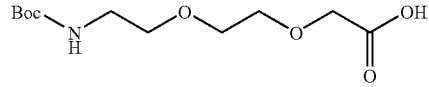

with about one equivalent of the acid protected bicine moiety (identified as 1 in FIG. 1) to form an intermediate such as:

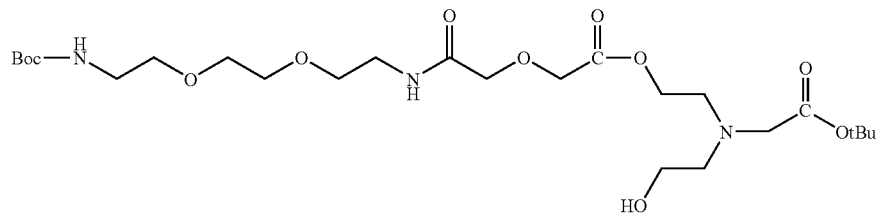

where tBu is a protecting group;

2) reacting the intermediate of step 1) with an acylating agent such as, for example, acetyl chloride, to form an intermediate such as:

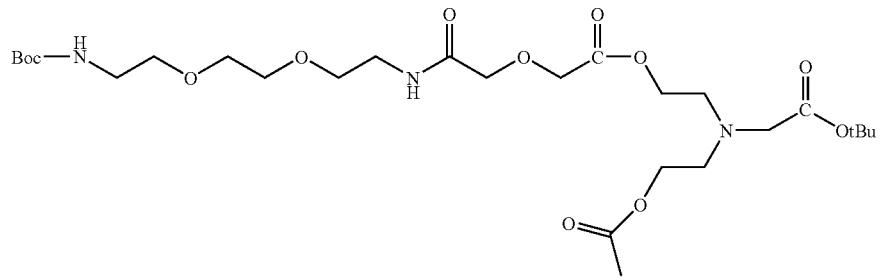

3) deblocking the resultant intermediate above and reacting it with an activated polymer such as PNP-PEG or SC-PEG under basic coupling conditions, 4) deprotecting the bicine acid and thereafter activating the acid with a suitable activating group such as thiazolidinyl thione or N-hydroxylsuccinimide, under coupling conditions.

An alternative method for making the bicine derivatives includes:

1) reacting one equivalent of an extended blocked bifunctional linker with one equivalent of the acid protected bicine moiety to form an intermediate such as:

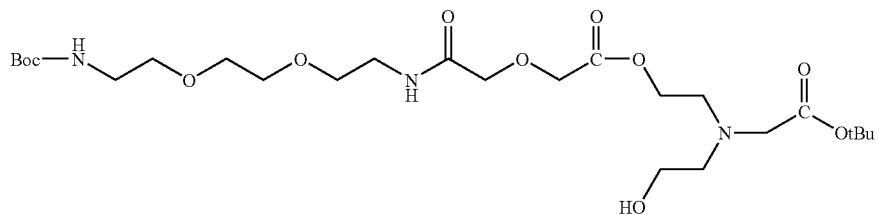

where tBu is a protecting group;

2) reacting the intermediate from step 1) with an appropriately modified activating group such as

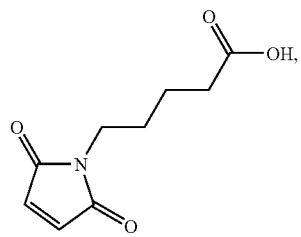

to form an intermediate such as:

3) deblocking the resultant intermediate above and reacting it with an activated polymer such as PNP-PEG or SC-PEG under basic coupling conditions, and 4) deprotecting the bicine acid and thereafter activating the acid with a suitable activating group such as thiazolidinyl thione or N-hydroxylsuccinimide, under coupling conditions.

It will be understood that other art recognized protecting groups can be used in place of t-Bu. The activated PEG or polymer bicine derivative is now capable of reacting with and conjugating to a drug, peptide, spacer, etc.

A non-limiting list of suitable coupling agents include 1,3-diisopropyl-carbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as tetrahydrofuran (THF), acetonitrile ($CH_3CN$), methylene chloride (DCM), chloroform ($CHCl_3$), dimethyl formamide (DMF) or mixtures thereof. Suitable bases include dimethylaminopyridine (DMAP), diisopropylethylamine, pyridine, triethylamine, KOH, potassium t-butoxide and NaOH etc. The reactions are usually carried out at a temperature of from about 0° C. up to about 22° C. (room temperature).

Regardless of the route selected, some of the preferred compounds which result from the synthetic techniques described herein include:

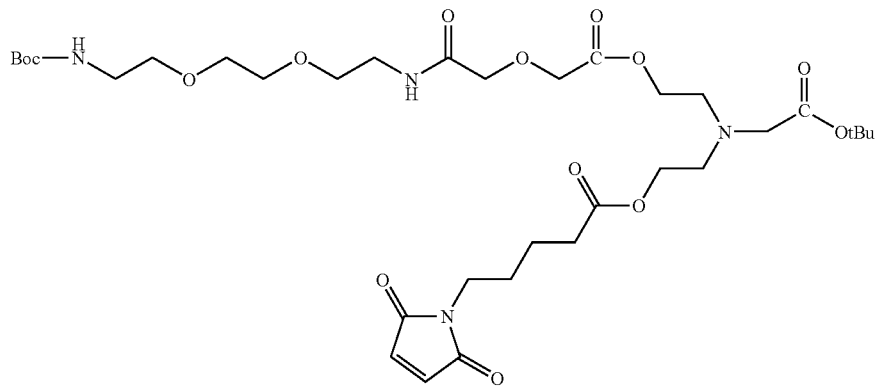

(Ia)
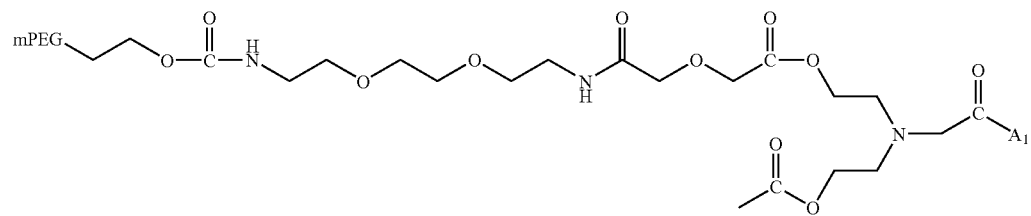
(Ib)
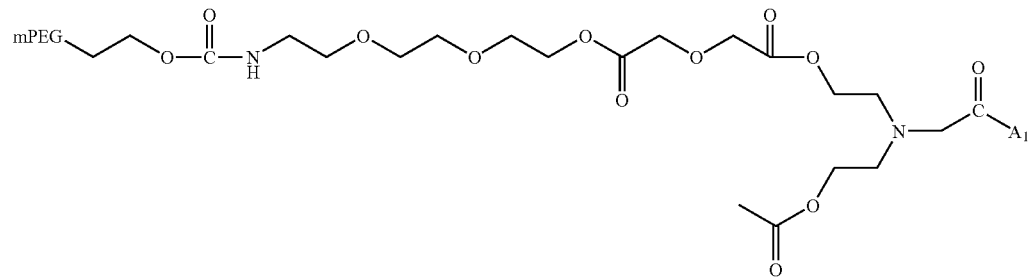
(Ic)
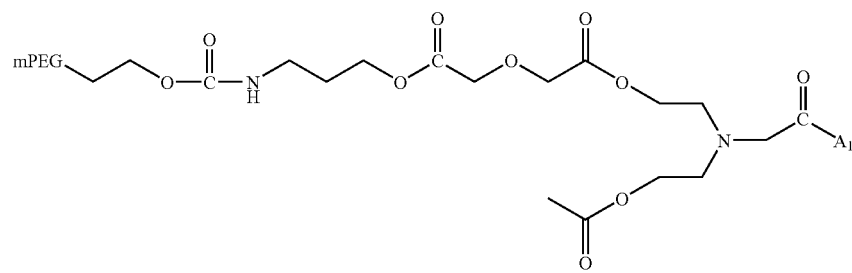
(Id)
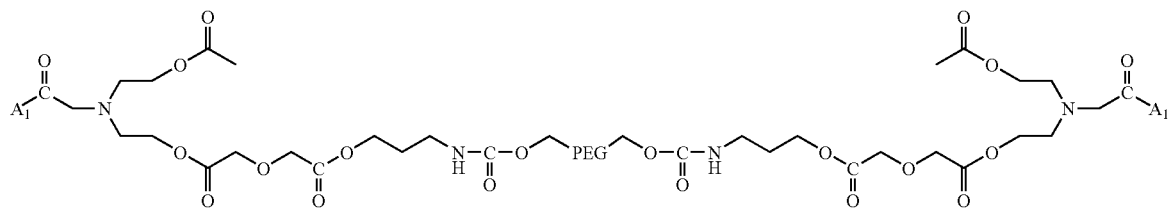
(Ie)
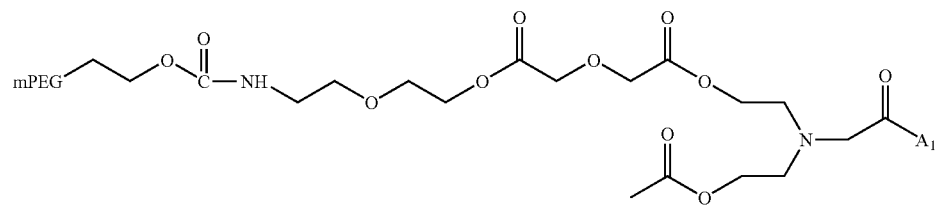
(If)
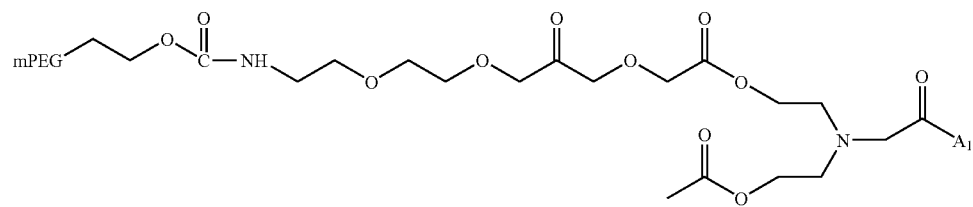

-continued
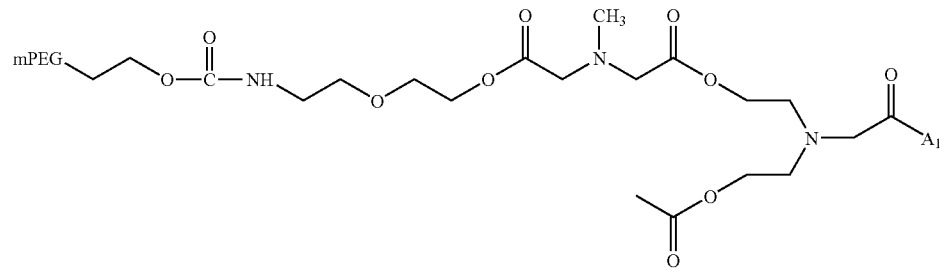
(Ig)
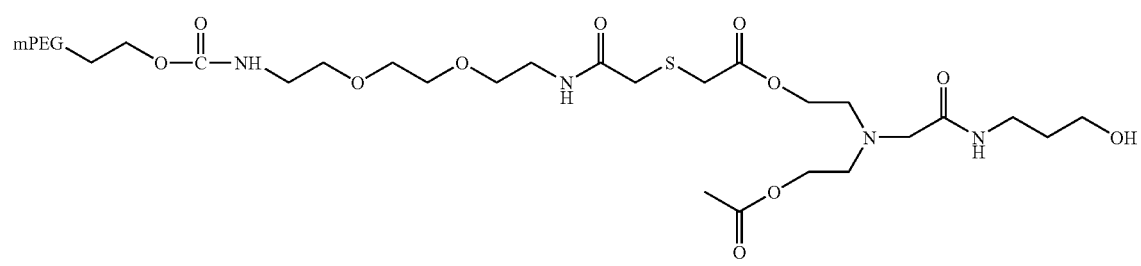
(Ih)
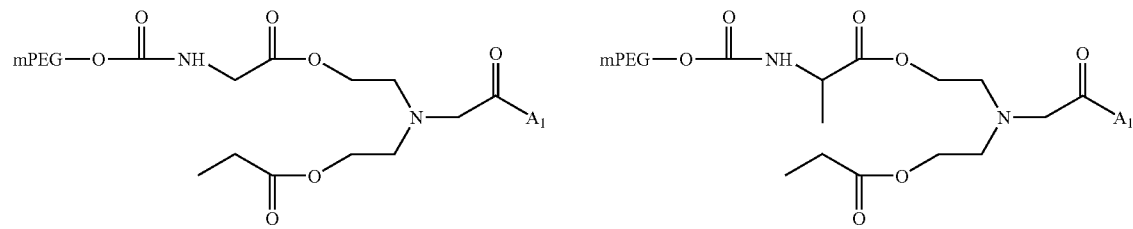
(Ii) (Ij)
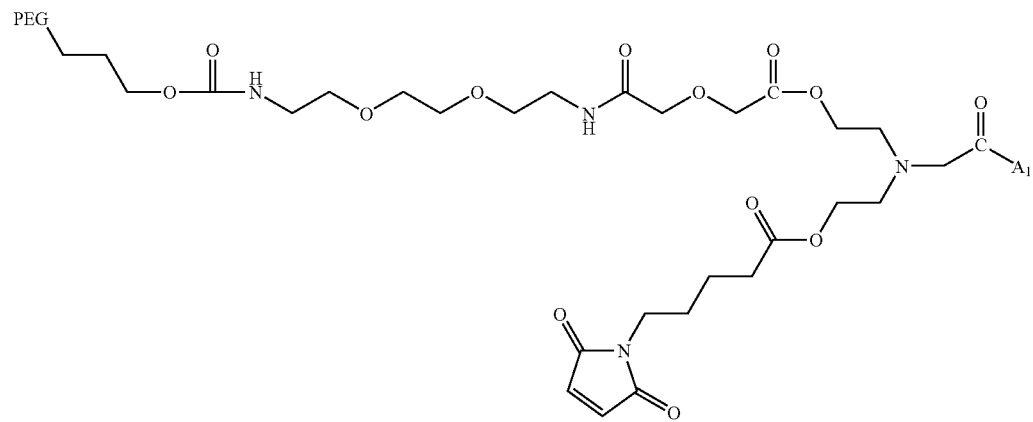
(Ik)
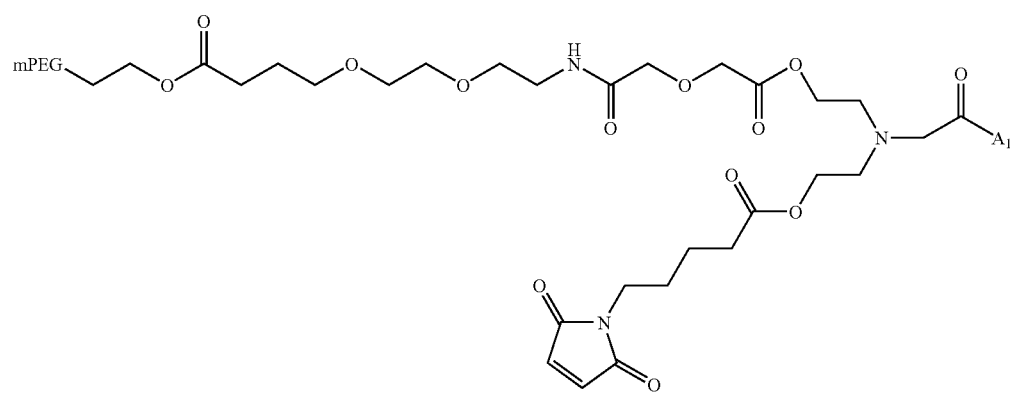
(Im)

where $A_1$ is a group such as:

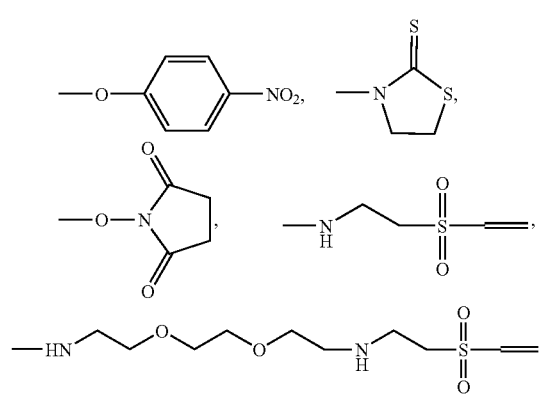

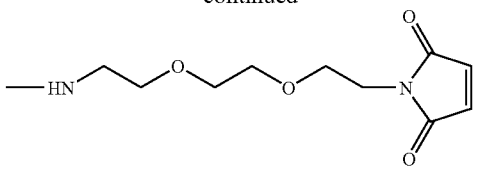

or other leaving or activating groups such as those described above.

Reaction of the bicine-activated polymers with a suitable target results in the transformation of the activated polymer into conjugates, transforming $A_1$ into $A_2$, were $A_2$ is a residue of a biologically active moiety, spacer, etc.

A non-limiting list of preferred compounds that result from the techniques described herein above are:

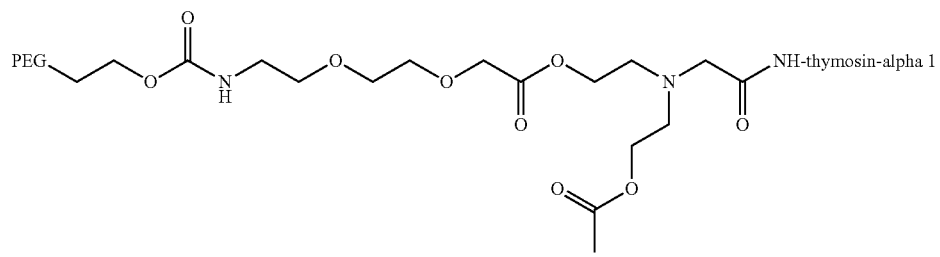

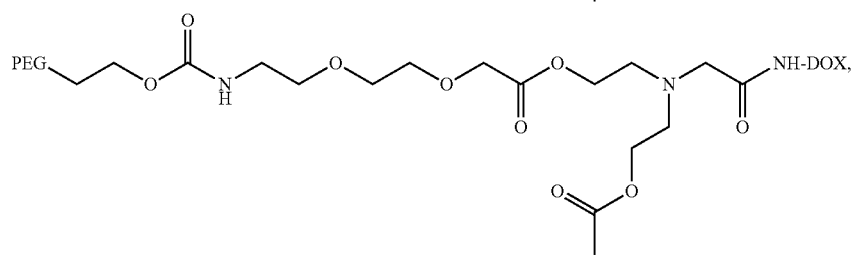

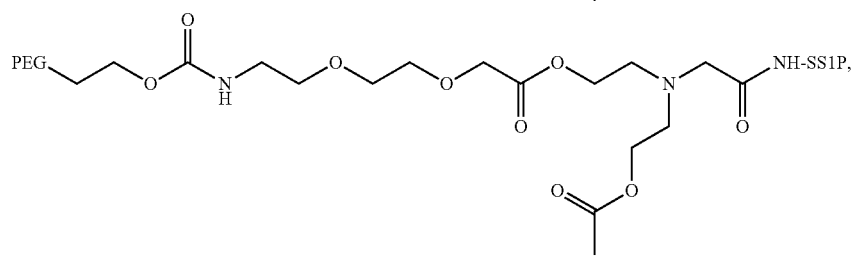

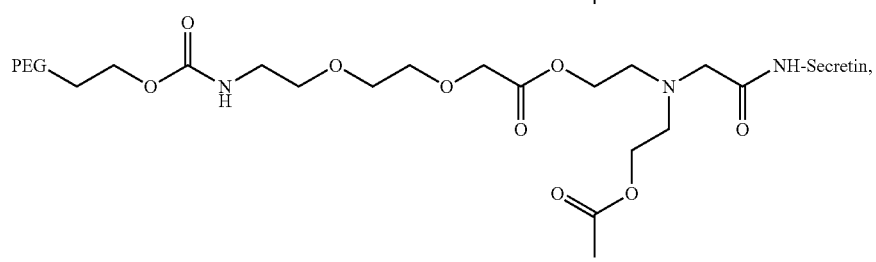

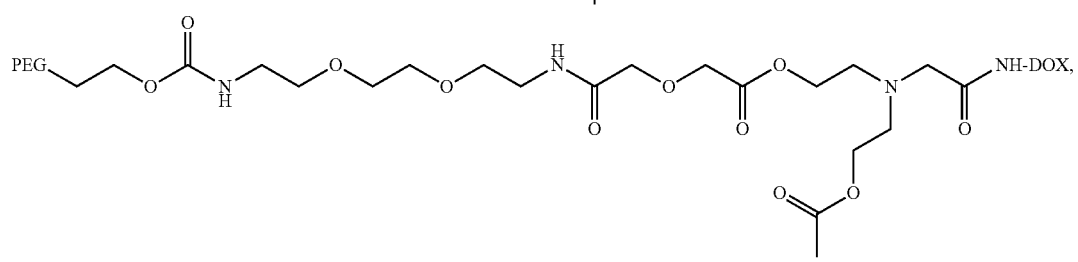

-continued

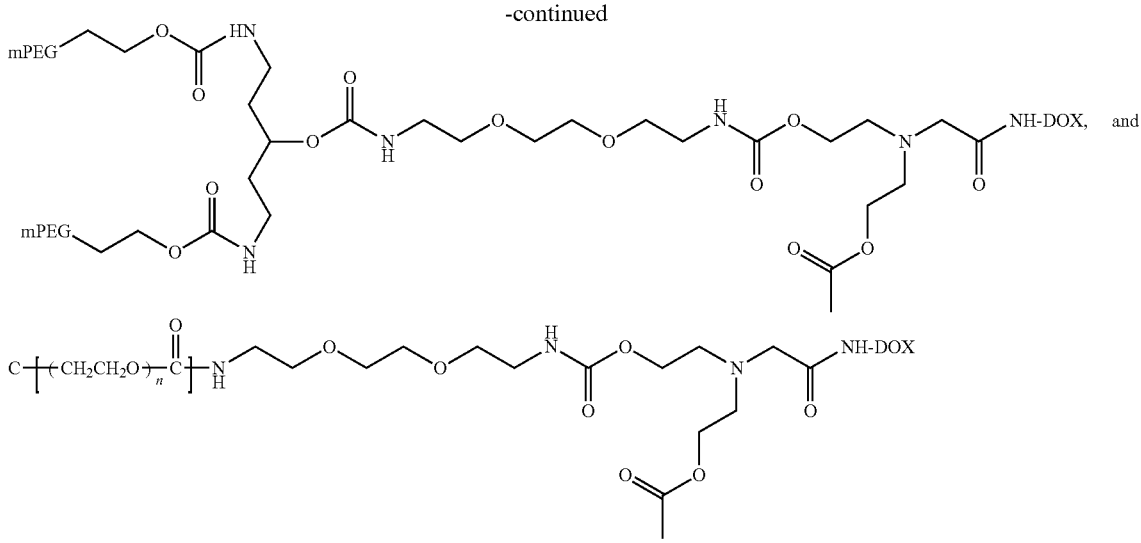

wherein:

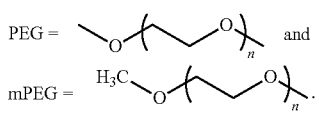

G. Multiple Polymer Loading

In a still further aspect of the invention there are provided bicine-based multiple branched polymer compounds. In particular, the base bicine derivative is further modified to include one or more terminal branching groups. Preferably, the terminal branching groups are of the formula:

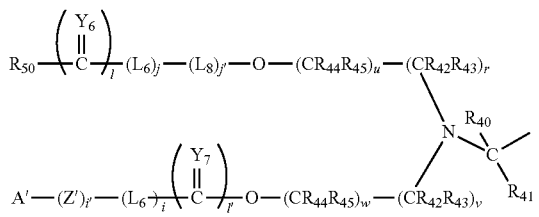

wherein:
$Y_6$ and $Y_7$ are independently O, S or $NR_{46}$;
$L_6$ is a bifunctional linker selected from the same group as that which defines $L_1$;
$L_8$ is a bifunctional linker selected from the same group as that which defines $L_2$;
$R_{40}$-$R_{46}$ may be the same or different and are selected from the group consisting of hydrogen, $C_{1-6}$ alkyls, $C_{2-6}$ alkenyl, $C_{2-6}$ alkynyl, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
j, j', i and i' are each independently 0 or a positive integer;
l and l' are independently 0 or 1;
u, r, v and w are independently selected positive integer-s;
$R_{50}$ is selected from the group consisting of substantially non-antigenic polymer residues,
$C_{1-6}$ alkyls, $C_{2-6}$ alkenyl, $C_{2-6}$ alkynyl, aralkyls, and

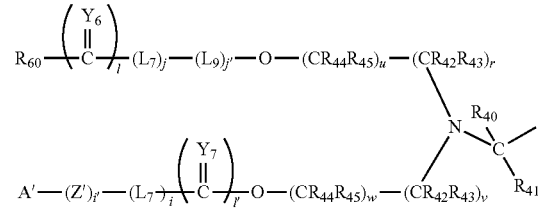

wherein:
$L_7$ is a bifunctional linker selected from the same group as that which defines $L_1$;
$L_9$ is a bifunctional linker selected from the same group as that which defines $L_2$;
$R_{60}$ is selected from the group consisting of substantially non-antigenic polymer residues, $C_{1-6}$ alkyls, $C_{2-6}$ alkenyl, $C_{2-6}$ alkynyl, aralkyls, and
all other variables are as defined above.

The resulting branched bicine derivatives are of the formula stricture:

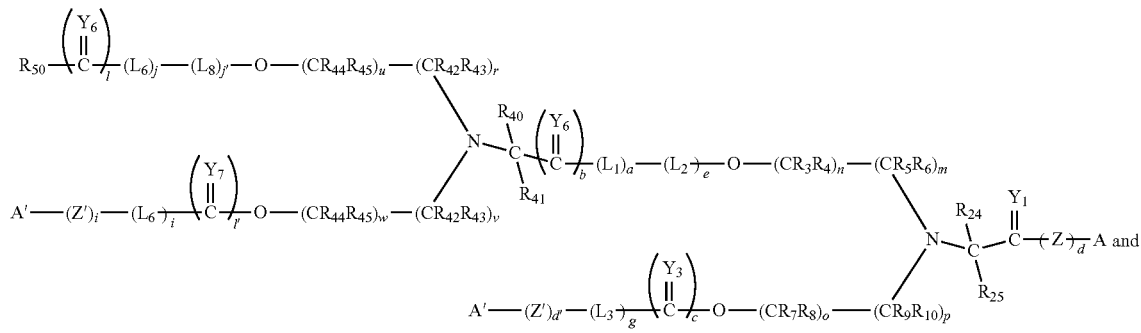

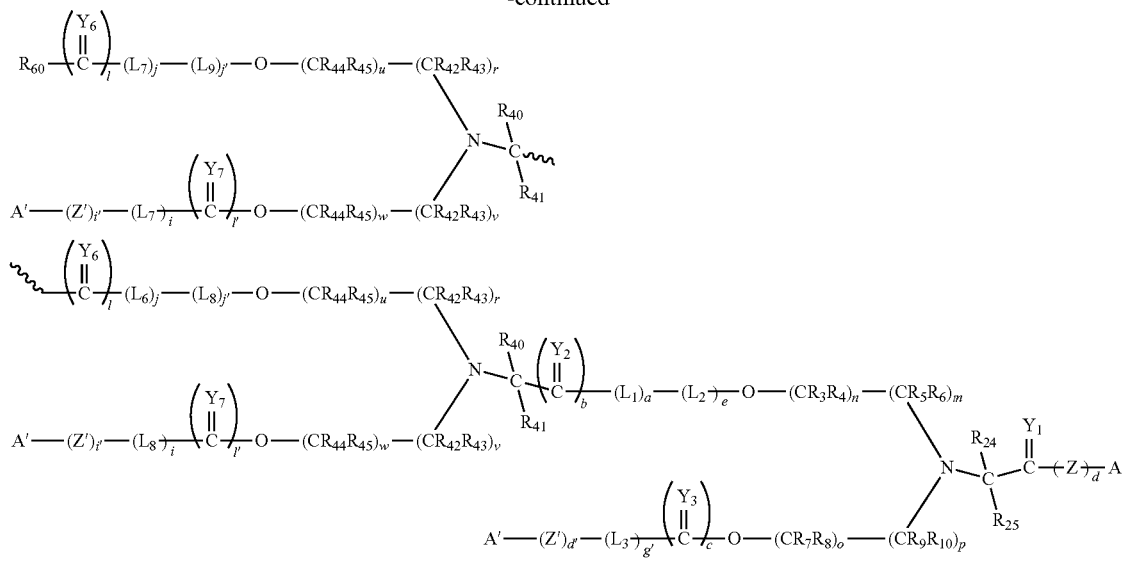

where all variables are as previously defined above.

As demonstrated above and in the examples, the bicine polymer systems formed using the methods of this invention provide for the ability for multiple loading of biologically active moieties or other A groups. An advantage of this branched bicine system of the present invention is that the artisan can employ a linear high molecular weight polymer and in addition, attach one or more biologically active moieties, diagnostic agents or targeting agents in a variety of combinations according to the needs of the artisan.

H. In Vivo Diagnostics

Another aspect of the invention provides for conjugates of the invention optionally prepared with a diagnostic tag linked to the transport enhancer described above, wherein the tag is selected for diagnostic or imaging purposes. Thus, a suitable tag is prepared by linking any suitable moiety, e.g., an amino acid residue, to any art-standard emitting isotope, radioopaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radioimmunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888,474; 5,997,844; and 5,997,845, incorporated by reference herein.

Broadly, for anatomical localization of tumor tissue in a patient, the conjugate tag is administered to a patient or animal suspected of having a tumor. After sufficient time to allow the labeled immunoglobulin to localize at the tumor site(s), the signal generated by the label is detected, for instance, visually, by X-ray radiography, computerized trans-axial tomography, MRI, by instrumental detection of a luminescent tag, by a photo scanning device such as a gamma camera, or any other method or instrument appropriate for the nature of the selected tag.

The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

I. Methods of Treatment

Another aspect of the present invention provides methods of treatment for various medical conditions in mammals. The methods include administering to the mammal in need of such treatment, an effective amount of a prodrug, such as a doxorubicin-bicine linked-PEG conjugate, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule, e.g., peptide, polypeptide, protein, enzyme, etc. included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. Those skilled in the art will determine the optimal dosing of the prodrug selected based on clinical experience and the treatment indication. Actual dosages will be apparent to the artisan without undue experimentation.

The compositions of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

EXAMPLES

The following examples serve to provide further appreciation of the invention but are not meant in any way to restrict the effective scope of the invention. The underlined and bold-faced numbers recited in the Examples correspond to those shown in FIGS. 1 to 5.

Chemistry

General Procedures. All reactions were run under an atmosphere of dry nitrogen or argon. Commercial reagents were used without further purification. All PEG compounds were dried under vacuum or by azeotropic distillation from toluene prior to use. NMR spectra were obtained using a Varian Mercury® 300 NMR spectrometer and deuterated chloroform as the solvent unless otherwise specified. Chemical shifts ($\delta$) are reported in parts per million (ppm) downfield from tetramethylsilane (TMS).

HPLC method. The reaction mixtures and the purity of intermediates and final products were monitored by a Beckman Coulter System Gold® HPLC instrument employing a ZOBAX® 300 SB C-8 reversed phase column (150×4.6 mm) or a Phenomenex Jupiter® 300A C18 reversed phase column (150×4.6 mm) with a multiwavelength UV detector, using a gradient of 30-90% of acetonitrile in 0.5% trifluoroacetic acid (TFA) at a flow rate of 1 mL/min.

Example 1

Synthesis of Compound 3

A solution of 2 (2.3 g, 8.7 mmol), 1 (1.9 g, 8.8 mmol), and DMAP (1.6 g, 12.9 mmol) in 30 ml of dry methylene chloride was cooled to 0° C. in an ice bath, followed by addition of EDC hydrochloride (2.3 g, 12.0 mmol). This mixture was allowed to warm to room temperature overnight, followed by washing with 0.1 N HCl. The organic layer was dried over anhydrous sodium sulfate, filtered, and the solvent removed from the filtrate by rotovap to yield 3 (3.6 g, 7.8 mmol, 90%). $^{13}$C NMR (75.4 MHz, CDCl$_3$) d 170.04, 169.86, 155.54, 80.87, 78.66, 70.49, 69.95, 68.14, 62.71, 55.85, 52.59, 40.02, 28.15, 27.91.

Example 2

Synthesis of Compound 4

To a solution of 3 (1.8 g, 3.9 mmol) in 35 ml of dry methylene chloride was added acetyl chloride (0.49 g, 6.2 mmol), followed by diisopropylethyl amine (1.82 g, 14 mmol). This mixture was stirred for 10 minutes at room temperature, at which time no starting material was detected by TLC. This mixture was washed with saturated sodium bicarbonate and dried over anhydrous sodium sulfate, filtered, and the solvent removed from the filtrate by rotovap to yield 1.6 g of crude product. This material was purified by column chromatography on silica gel and eluted with 2.5% acetonitrile in ethyl acetate to yield 4 (0.69 g, 1.4 mmol, 35%). $^{13}$C NMR (75.4 MHz, CDCl$_3$) d 170.60, 170.27, 170.02, 155.68, 80.99, 78.88, 70.68, 70.13, 70.10, 68.34, 62.93, 62.74, 56.11, 52.81, 52.76, 40.21, 28.29, 28.08, 20.88.

Example 3

Synthesis of Compound 7

A solution of 4 (0.25 g, 0.50 mmol) in 20 ml of methylene chloride and 5 ml of TFA, was stirred for 15 minutes at room temperature, followed by removal of the solvents by rotovap to yield 5. Compound 5 was combined with 10 ml of dry methylene chloride, followed by addition of DIEA until the pH was above 8.0 (~0.2 g). This bicine solution was added to a solution of 6 (5.0 g, 0.12 mmol) in 40 ml of dry methylene chloride, and stirred overnight at room temperature. At this time, the solvent was partially removed by rotovap, the product precipitated with ether, and collected and washed with ether. This crude product was recrystallized from 12% DMF/IPA to yield 7 (4.6 g, 0.11 mmol, 90%).
$^{13}$C NMR (75.4 MHz, CDCl$_3$) d 170.31, 170.03, 169.76, 155.91, 80.74, 70.64-70.19 (PEG), 69.78, 69.72, 69.23, 68.13, 63.52, 62.73, 62.53, 55.92, 52.64, 40.46, 27.91, 20.69.

Example 4

Synthesis of Compound 8

A solution of 7 (4.8 g, 0.12 mmol) in 50 ml of methylene chloride and 25 ml of TFA was stirred for 7 hrs at room temperature, followed by partial removal of the solvent by rotovap, and precipitation of the product with ether. The solid was collected by filtration, and washed several times with ether and dried to yield 8 (4.1 g, 0.10 mmol, 85%). $^{13}$C NMR (75.4 MHz, CDCl$_3$) d 171.15, 170.25, 169.71, 155.96, 70.19-69.77 (PEG), 69.22, 69.16, 63.51, 62.29, 61.94, 55.77, 53.11, 53.01, 40.44, 20.60.

Example 5

Synthesis of Compound 9

A solution of 8 (4.0 g, 0.1 mmol), 2-mercaptothiazoline (70 mg, 0.59 mmol), and DMAP (0.1 g, 0.79 mmol) in 40 ml of dry methylene chloride was cooled to 0° C. in an ice bath, followed by addition of EDC hydrochloride (0.11 g, 0.59 mmol). This mixture was allowed to warn to room temperature overnight. At this time, the solvent was partially removed by rotovap, the product precipitated with ether, and collected and washed with ether. This crude product was recrystallized from 12% DMF/IPA to yield 9 (3.7 g, 0.09 mmol, 93%). $^{13}$C NMR (75.4 MHz, CDCl$_3$) d 200.96, 172.78, 170.35, 169.80, 155.93, 70.70-70.21 (PEG), 69.81, 69.75, 69.25, 68.13, 63.57, 63.03, 62.77, 60.64, 55.34, 52.64, 40.49, 28.80, 20.72.

Example 6

Synthesis of Compound 10

A solution of 9 (3.0 g, 0.073 mmol), doxorubicin (0.17 g, 0.29 mmol) and DMAP (71 mg, 0.59 mmol) in 30 ml of methylene chloride and 30 ml of DMF was stirred overnight at room temperature. At this time, the solvent was partially removed by rotovap, the product precipitated with ether, and collected and washed with ether. This crude product was recrystallized three times from DMF/IPA to yield 10 (2.9 g, 0.069 mmol, 94%). $^{13}$C NMR (75.4 MHz, CDCl$_3$) d 211.24, 186.23, 185.89, 170.47, 169.82, 169.04, 161.81, 160.34, 155.78, 155.14, 135.20, 134.79, 133.84, 133.58, 120.16, 119.13, 118.01, 110.76, 110.60, 100.34, 72.19-67.95 (PEG), 66.87, 63.31, 61.75, 61.45, 58.97, 56.21, 53.83, 44.44, 40.29, 36.03, 34.67, 32.83, 30.97, 29.38, 24.97, 24.45, 20.54, 16.46.

Example 7

Synthesis of Compound 13

A solution of 12 (2.5 g, 10.1 mmol), diglycolic anhydride 11 (1.1 g, 9.5 mmol) and DMAP (1.3 g, 9.5 mmol) in 25 ml of methylene chloride was stirred overnight at room temperature, followed by washing with 0.2 N HCl. The organic layer was dried over anhydrous sodium sulfate, filtered, and the solvent removed from the filtrate by rotovap to yield 13 (2.9 g, 8.0 mmol, 84%). Nmr showed peak doubling. $^{13}$C NMR (75.4 MHz, CDCl$_3$) d 172.92, 171.14, 169.92, 169.58, 157.50, 155.79, 80.86, 79.03, 71.34, 70.69, 70.19, 70.06, 69.84, 69.64, 69.33, 69.15, 68.85, 68.40, 53.29, 41.37, 36.97, 38.75, 38.55, 28.10.

Example 8

Synthesis of Compound 14

A solution of 13 (2.8 g, 7.7 mmol), 1 (1.7 g, 7.7 mmol), and DMAP (1.3 g, 10.8 mmol) in 30 ml of dry methylene chloride was cooled to 0° C. in an ice bath, followed by addition of 1.9 g (10.0 mmol) of EDC hydrochloride. This mixture was allowed to warm to room temperature overnight, followed by washing with 0.2 N HCl. The organic layer was dried over anhydrous sodium sulfate, filtered, and the solvent removed from the filtrate by rotovap to yield 14 (2.3 g, 4.1 mmol, 53%).

Example 9

Synthesis of Compound 15

To a solution of crude 14 (2.3 g, 4.1 mmol) in 20 ml of dry methylene chloride was added acetyl chloride (0.64 g, 8.2 mmol), followed by diisopropylethyl amine (1.1 g, 8.2 mmol). This mixture was stirred for 10 minutes at room temperature, at which time no starting material was detected by TLC. This mixture was washed with saturated sodium bicarbonate and dried over anhydrous sodium sulfate, filtered, and the solvent removed from the filtrate by rotovap to yield 2.1 g of crude product. This material was purified by column chromatography on silica gel and eluted with 5% methanol in ethyl acetate to yield (0.24 g, 0.40 mmol, 10%). $^{13}$C NMR (75.4 MHz, CDCl$_3$) d 170.33, 170.02, 169.17, 168.44, 155.47, 80.78, 78.64, 70.64, 69.81, 69.26, 68.07, 63.01, 62.48, 55.92, 52.57, 40.00, 38.31, 28.10, 27.87, 20.65.

This acetylated product (0.23 g, 0.38 mmol) was stirred for 15 minutes in a solution of 20 ml of methylene chloride and 5 ml of TFA, followed by removal of the solvents by rotovap. This bicine residue was combined with 10 ml of dry methylene chloride, followed by addition of DIEA until the pH was above 8.0 (~0.2 g). This bicine solution was added to a solution of 6 (4.0 g, 0.10 mmol) in 30 ml of dry methylene chloride, and stirred overnight at room temperature. At this time, the solvent was partially removed by rotovap, the product precipitated with ether; and collected and washed with ether. This crude product was recrystallized from 12% DMF/IPA to yield (3.8 g, 0.02 mmol, 95%).

$^{13}$C NMR (75.4 MHz, CDCl$_3$) d 170.29, 169.97, 169.13, 168.37, 155.90, 80.80, 70.68-69.67 (PEG), 69.20, 68.09, 63.52, 63.02, 62.47, 55.94, 52.59, 40.49, 38.31, 27.91, 20.69.

A solution of this PEGylated product (3.8 g, 0.10 mmol) in 40 ml of methylene chloride and 20 ml of TFA was stirred for 15 has at room temperature, followed by partial removal of the solvent by rotovap, and precipitation of the product with ether. The solid was collected by filtration, and washed several times with ether and dried to yield the acid (3.4 g, 0.08 mmol, 89%). $^{13}$C NMR (75.4 MHz, CDCl$_3$) d 170.96, 169.93, 168.89, 168.23, 155.78, 72.45-66.94 (PEG), 63.23, 62.38, 61.63, 54.82, 52.47, 40.23, 38.03, 20.39.

A solution of this acid (3.4 g, 0.08 mmole), 2-mercaptothiazoline (59 mg, 0.50 mmol), and DMAP (81 mg, 0.66 mmol) in 40 ml of dry methylene chloride was cooled to 0° C. in an ice bath, followed by addition of EDC hydrochloride (0.11 g, 0.59 mmol). This mixture was allowed to warm to room temperature overnight. At this time, the solvent was partially removed by rotovap, the product precipitated with ether, and collected and washed with ether. This crude product was recrystallized from 20% DMF/IPA to yield 15 (3.2 g, 0.078 mmol, 94%). $^{13}$C NMR (75.4 MHz, CDCl$_3$) d 200.96, 172.64, 170.28, 168.13, 168.34, 155.85, 75.76-69.15 (PEG), 68.07, 63.48, 63.20, 62.62, 60.56, 55.31, 52.53, 40.44, 38.26, 28.74, 20.66.

Example 10

Synthesis of Compound 16

A solution of 15 (3.2 g, 0.0783 mmol), doxorubicin (0.18 g, 0.319 mmol) and DMAP (77 mg, 0.62 mmol) in 30 ml of methylene chloride and 30 ml of DMF was stirred overnight at room temperature. At this time, the solvent was partially removed by rotovap, the product precipitated with ether, and collected and washed with ether. This crude product was recrystallized four times from 20% DMF/IPA to yield 16 (2.8 g, 0.067 mmol, 88%). $^{13}$C NMR (75.4 MHz, CDCl$_3$) d 212.98, 186.21, 185.86, 170.34, 169.33, 168.98, 168.29, 160.32, 155.79, 155.58, 154.94, 135.22, 134.70, 133.23, 133.05, 120.09, 119.14, 118.03, 110.79, 110.61, 100.29, 75.90-68.44 (PEG), 67.80, 66.91, 64.90, 663.31, 62.06, 61.36, 58.79, 56.18, 53.86, 53.60, 44.37, 40.26, 38.12, 35.25, 33.27, 29.33, 20.47, 16.48.

Example 11

Synthesis of Compound 17

To a solution of 12 (1.0 g, 4.0 mmol) in 20 ml of methylene chloride at room temperature was added triphosgene (0.4 g, 1.3 mmol), and diisopropylethyl amine (1.0 g, 8.1 mmol). This mixture was stirred for one hour at room temperature, followed by addition of 1 (0.88 g, 4.0 mmol), and DMAP (0.5 g, 4.0 mmol). This mixture was left to stir overnight at room temperature, followed by washing with 0.1 N HCl. The organic layer was dried over anhydrous sodium sulfate, filtered, and the solvent removed from the filtrate by rotovap to yield 2.2 g of crude product. This material was purified by column chromatography on silica gel and eluted with 6% methanol in ethyl acetate to yield 17 (1.3 g, 2.6 mmol, 65%). $^{13}$C NMR (75.4 MHz, CDCl$_3$) d 170.86, 156.23, 155.69, 81.10, 78.94, 62.60, 59.03, 56.81, 56.09, 53.17, 40.68, 40.18, 28.28, 28.00.

Example 12

Syntheses of Compound 18

To a solution of 17 (0.1 g, 0.2 mmol) in 2 ml of dry methylene chloride was added acetyl chloride (32 mg, 0.4 mmol), followed by diisopropylethyl amine (87 min, 0.67 mmol). This mixture was stirred for 10 minutes at room temperature, at which time no starting material was detected by TLC. This mixture was washed with saturated sodium bicarbonate and dried over anhydrous sodium sulfate, filtered, and the solvent removed from the filtrate by rotovap to yield 18 (0.1 g, 0.2 mmol, 100%). $^{13}$C NMR (75.4 MHz, CDCl$_3$) d 170.59, 170.33, 156.16, 155.64, 80.99, 79.13, 70.21, 70.05, 63.08, 62.97, 56.48, 53.46, 52.92, 40.87, 40.39, 28.49, 28.27, 21.04, 20.69.

Example 13

Syntheses of Compound 20

A solution of 18 (0.1 g, 0.2 mmol) was stirred for 15 minutes in 8 ml of methylene chloride and 2 ml of TFA, followed by removal of the solvents by rotovap. This bicine residue was combined with 5 ml of dry methylene chloride, followed by addition of DMAP until the pH was above 8.0 (~0.6 g). This bicine solution was added to a solution of 19 (2.0 g, 0.05 mmol) in 15 ml of dry methylene chloride, and stirred overnight at room temperature. At this time, the solvent was partially removed by rotovap, the product precipitated with ether; and collected and washed with ether. This crude product was recrystallized from 12% DMF/IPA to yield 20 (1.8 g, 0.04 mmol, 90%). $^{13}$C NMR (75.4 MHz, CDCl$_3$) d 170.50, 170.18, 156.40, 156.37, 156.08, 155.32, 80.74, 71.57-65.23 (PEG), 63.72, 63.29, 62.62, 58.68, 56.10, 53.13, 52.53, 40.93, 40.51, 27.94, 20.74.

Example 14

Syntheses of Compound 21

A solution of 20 (1.8 g, 0.04 mmol) in 20 ml of methylene chloride and 10 ml of TFA was stirred for 7 hrs at room temperature, followed by partial removal of the solvent by rotovap, and precipitation of the product with ether. The solid was collected by filtration, and washed several times with ether and dried to yield (1.4 g, 0.03 mmol, 78%). $^{13}$C NMR (75.4 MHz, CDCl$_3$) d 172.11, 170.34, 156.39, 156.16, 155.41, 72.80-67.82 (PEG), 63.75, 63.35, 62.30, 61.89, 58.71, 56.15, 53.66, 53.25, 40.93, 40.55, 20.65.

A solution of this acid (1.2 g, 0.03 mmol), 2-mercaptothiazoline (0.01 g, 0.09 mmol), and DMAP (0.014 g, 0.12 mmol) in 10 ml of dry methylene chloride was cooled to 0° C. in an ice bath, followed by addition of EDC hydrochloride (0.017 g, 0.09 mmol). This mixture was allowed to warm to room temperature overnight. At this time, the solvent was partially removed by rotovap, the product precipitated with ether, and collected and washed with ether. This crude product was recrystallized from 12% DMF/IPA to yield 21 (1.1 g, 0.03 mmol, 92%). $^{13}$C NMR (75.4 MHz, CDCl$_3$) d 170.76, 170.46, 156.33, 155.99, 155.30, 71.54-69.12 (PEG), 63.69, 63.32, 62.84, 62.62, 60.70, 58.67, 55.36, 53.05, 52.49, 40.92, 40.49, 28.78, 20.71.

Example 15

Syntheses of Compound 22

A solution of 21 (1.0 g, 0.025 mmol), doxorubicin (28 mg, 0.05 mmol) and DMAP (12 mg, 0.1 mmol) in 10 ml of methylene chloride and 10 ml of DMF was stirred overnight at room temperature. At this time, the solvent was partially removed by rotovap, the product precipitated with ether, and collected and washed with ether. This crude product was recrystallized three times from 12% DMF/IPA to yield 22 (0.6 g, 0.015 mmol, 60%).

Example 16

Syntheses of Compound 24

A solution of 23 (23 g, 0.575 mmol) and disuccinimidyl carbonate (2.36 g, 9.2 mmol) in 230 ml of methylene chloride and 23 ml of DMF was cooled to 0° C., followed by the addition of pyridine (0.75 ml, 9.2 mmol). This mixture was allowed to warm to room temperature overnight, followed by filtration through Celite® and partial removal of the solvent from the filtrate by rotary evaporator. The crude product was precipitated out with ether and collected by filtration. Recrystallization from 20% DMF/IPA yielded 24 (20 g, 0.05 mmol, 86%). $^{13}$C NMR (75.4 MHz, CDCl$_3$) d 168.15, 151.14, 70.76-69.67 (PEG), 67.99, 45.24, 25.20.

Example 17

Syntheses of Compound 25

A solution of 18 (0.51 g, 0.9 mmol) was combined with 10 ml of dry methylene chloride, followed by addition of DIEA until the pH was above 8.0 (~0.6 g). This bicine solution was added to a solution of 24 (5.0 g, 0.12 mmol) in 40 ml of dry methylene chloride, and stirred overnight at room temperature. At this time, the solvent was partially removed by rotovap, the product precipitated with ether, and collected and washed with ether. This crude product was recrystallized from 12% DMF/IPA to yield 25 (4.9 g, 0.12 mmol, 94%). $^{13}$C NMR (75.4 MHz, CDCl$_3$) d 170.38, 170.12, 155.90 (d), 80.65, 72.16-69.20 (PEG), 63.51, 62.79, 62.62, 61.28, 56.12, 53.10, 52.53, 45.19, 40.46, 27.91, 20.72.

Example 18

Syntheses of Compound 26

A solution of 25 (5.5 g, 0.13 mmol) in 55 ml of methylene chloride and 28 ml of TFA was stirred for 7 hrs at room temperature, followed by partial removal of the solvent by rotovap, and precipitation of the product with ether. The solid was collected by filtration, and washed several times with ether and dried to yield the acid (5.1 g, 0.12 mmol, 93%). $^{13}$C NMR (75.4 MHz, CDCl$_3$) d 170.49, 170.20, 156.01, 155.68, 70.70-69.22 (PEG), 67.80, 66.68, 63.54, 62.64, 61.65, 61.22, 55.45, 53.57, 53.17, 45.21, 40.52, 20.56.

A solution of the acid (5.0 g, 0.12 mmol), 2-mercaptothiazoline (0.17 g, 1.4 mmol), and DMAP (0.23 g, 1.9 mmol) in 50 ml of dry methylene chloride was cooled to 0° C. in an ice bath, followed by addition of EDC hydrochloride (0.28 g, 1.5 mmol). This mixture was allowed to warm to room temperature overnight. At this time, the solvent was partially removed by rotovap, the product precipitated with ether, and collected and washed with ether. This crude product was recrystallized from 12% DMF/IPA to yield 26 (4.6 g, 0.11 mmol, 92%). $^{13}$C NMR (75.4 MHz, CDCl$_3$) d 200.88, 172.83, 170.38, 155.91, 72.15-69.20 (PEG), 63.51, 63.03, 62.82, 62.62, 61.26, 60.70, 55.34, 53.07, 52.52, 45.19, 40.47, 28.78, 20.71.

Example 19

Synthesis of Compound 27

A solution of 26 (2.3 g, 0.055 mmol), doxorubicin (0.25 g, 0.44 mmol) and DMAP (0.11 g, 0.88 mmol) in 20 ml of methylene chloride and 20 ml of DMF was stirred overnight at room temperature. At this time, the solvent was partially removed by rotovap, the product precipitated with ether, and collected and washed with ether. This crude product was recrystallized twice from 12% DMF/IPA to yield 27 (1.7 g, 0.039 mmol, 71%).

Example 20

Preparation of Mono Bicine-12K-Lysozyme and Mono Bicine-20K-Lysozyme Conjugates

With fast stirring, PEG powder, at the reaction molar ratio of 1:1.5-2 of PEG to protein, was added to 6 ml of 5 mg/ml lysozyme (Sigma, Mo.) in 0.05 M sodium phosphate, pH 7.6. After 60 min. with the reaction temperature at 25° C. and under N$_2$, the sample was diluted with 10 mM sodium phosphate, pH 5.1 to conductivity lower than 2 ms, pH ~5 (the lower pH would quench the reaction and stabilize the releasable PEG-protein conjugate).

Mono PEG-lysozyme was isolated on a cation exchange column (Poros HS, Applied Biosystems, California) using a solvent system of 20 mM sodium phosphate, pH 5.1 and a gradient buffer of 1 M NaCl in 20 mM sodium phosphate, pH 5.1. The sequence of the compounds eluted out from the column was shown as multi PEG-lysozyme first, then mono PEG-lysozyme, and then native lysozyme. The peak of mono PEG-lysozyme identified on SDS-PAGE (precast 4-20% SDS non-reducing gel, Invitrogen, California) was collected and concentrated using the Ultrafree centrifugal filter device with 5 k NMWL membrane (Millipore Corp., Bedford, Mass.).

Example 21

Preparation of Multi Bicine-12K-Lysozyme and Multi Bicine-20K-Lysozyme Conjugates With fast stirring, PEG powder, at 1.20-30 reaction molar ratio of PEG to protein, was added to 0.5 ml of 5 mg/ml lysozyme in 0.1 M sodium phosphate, pH 7.6. The reaction was conducted at R.T. under N$_2$ for 60 mm and stopped by lowering pH to 6.0 or immediately purified on a size exclusion column.

The reaction mixture was diluted with 20 mM sodium phosphate, pH 6.0 to 5 ml, filtered through 0.45 µm filter, and separated on HiLoad Superdex 200 column (Amersham, N.J.). The column was equilibrated in 140 nl NaCl, 20 mM NaP, pH 6.0 and the conjugate was eluted out at 1 ml/fraction/min. The f-actions of the peak identified on SDS-PAGE were pooled and concentrated using Ultrafree 30K (Millipore Corp., Bedford, Mass.).

Example 22

In Vitro Results

TABLE 1

Properties of PEG-Bicine-Doxorubicin Conjugates

| Compound | $t_{1/2}$ (rp) h | mw | % Active |
|---|---|---|---|
| 10 | 4.8 | 41803 | 2.60 |
| 16 | 5.0 | 41554 | 2.34 |
| 22 | 56 | 41204 | 0.73 |
| 27 | 247 | 43722 | 4.25 |

Example 23

Protein Conjugation

Materials and Methods

Chicken egg white lysozyme (EC 3.2.1.17), lysozyme substrate bacteria (*Micrococcus lysodeikticus*), and PBS buffer (10 mM phosphate, pH 7.4, 138 mM NaCl, and 2.7 in M KCl) were purchased from Sigma Inc. (St. Louis, Mo.). Pre-cast Tris-glycine SDS electrophoresis gel and the gel running buffer were obtained from Invitrogen (Carlsbad, Calif.). Rat plasma used to measure in vitro hydrolyses of the conjugates was processed in EDTA aid stored frozen. IL-2 was purchased from PeproTech (Princeton, N.J.), and GFP was obtained from Clontech (Palo Alto, Calif.). All in vivo measurements were done in triplicate, and a standard deviation of ±5% was found for in vitro measurements.

Preparation of Single PEG-Lysozyme Conjugates

Lysozyme from chicken eggs has a molecular weight of 14,500 and 6 lysine residues. With fast stirring, the activated PEG powder, at a reaction molar ratio of 1:1 (PEG:lysozyme), was added to a lysozyme solution of 5 mg/mL in 0.1 M phosphate buffer, pH 7.3. After stirring for 45 min at 25° C., the reaction was treated with 0.2 M sodium phosphate (pH 5.1) to a final pH of 6.5. The reaction mixture was dialyzed against 20 mM sodium phosphate, pH 5.1, at 4° C., using 6,000-8,000 MW cutoff membrane. The sample conductivity after dialysis should be less than 2 mS. The isolation of single PEG-lysozyme was performed on a cation exchange column (Poros, HS) using a solvent system of 20 mM sodium phosphate at pH 5.1 with a NaCl gradient. The peak of single PEG-lysozyme was collected and concentrated using the ultrafree centrifugal filter device with 10 k NMWL membrane (Millipore Corp., Bedford, Mass.). The yield of the purified single PEG-lysozyme was about 20-30%.

Preparation of Multi PEG-Lysozyme Conjugates

With fast stirring, the activated PEG linker, at a reaction molar ratio of 30:1 (PEG:lysozyme), was added to a lysozyme solution of 5 mg/mL in 0.1 M phosphate buffer, pH 7.3. After stirring 45 min at room temperature, the reaction was treated with 0.2 M sodium phosphate (pH 5.1) to final pH of 6.5. The reaction mixture was diluted with H$_2$O and separated on Hiload Superdex 200 column at 1 mL/mini. The column buffer contains 20 mM sodium phosphate (pH 6.8) and 140 mM NaCl. The fractions of the peak were pooled and concentrated using the ultrafree centrifugal filter device with 30 k NMWL membrane (Millipore Corp., Bedford, Mass.). The yield of the purified multi PEG-lysozyme was about 85% and the PEG number per lysozyme molecule as analyzed by fluorometric assay was found to be 5-6.

Concentration Determination

PEG-lysozyme conjugate concentration was determined by UV using an extinction coefficient of 2.39 mL/mg·cm at 280=n in 0.1 M sodium phosphate, pH 7.3.

Enzyme Activity Assay for Lysozyme

Under the reaction conditions mentioned above, lysozyme activity disappeared after conjugation with only a single PEG. The release of the lysozyme was indicated by regeneration of the lysozyme activity under various release conditions and confirmed on SDS electrophoresis gel. In a typical lysozyme activity assay, 0.2 mL of 0.02% (w/v) *M. lysodeikticus* (substrate) was added to 0.12-0.24 µg of lysozyme in 50 µL 66 mM potassium phosphate, pH 6.2 containing 0.01% BSA, in a 96-well titer plate. The absorbance at 450 nm was followed for 5 min. The rate of decrease in absorbance was used as a measure of enzyme activity. One unit of enzyme activity produces a change of 0.001 absorbance units/min at 25° C. at 450 nm.

Release of Lysozyme in Rat Plasma and in Chemical Buffer

PEG-lysozyme conjugates in phosphate buffer, pH 6.5, underwent buffer exchange with PBS, pH 7.4, to monitor release in rat plasma. The stability in PBS at 37° C. was measured. The conjugates also underwent buffer exchange with $H_2O$ for the release in Tris buffer, pH 8.5. CentriCon 10 K centrifuge tube (Millipore Corp., Bedford, Mass.) was used for the single PEG-lysozyme conjugates while CentriCon 30K was used for the multi PEG-lysozyme conjugates. The release of lysozyme from single or multi PEG-lysozyme conjugates was conducted at 0.15 mg/mL, under $N_2$. At the time indicated, an aliquot was withdrawn, neutralized with 0.2 M phosphate (pH 5.1) to pH 6.5, and stored at −20° C. until further analysis.

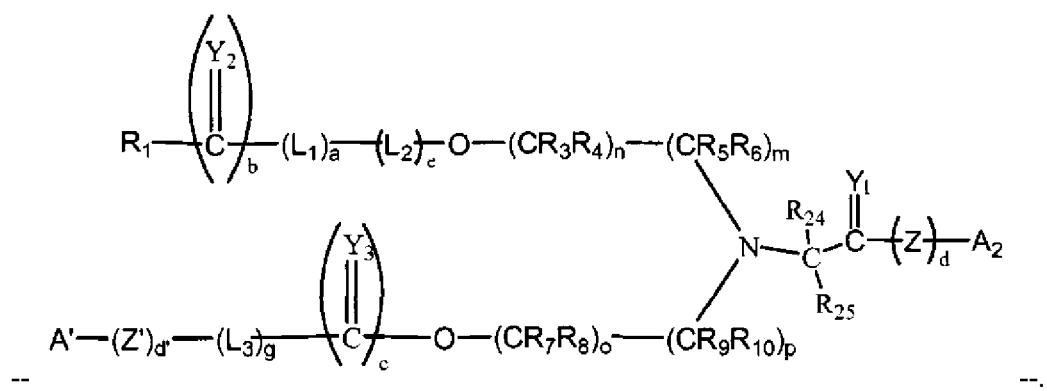

We claim:

1. A compound comprising Formula (I):

$$R_1 - \left(\overset{Y_2}{\underset{\|}{C}}\right)_b - (L_1)_a - (L_2)_e - O - (CR_3R_4)_n - (CR_5R_6)_m \cdots$$

$$A'-(Z')_{d'}-(L_3)_g-\left(\overset{Y_3}{\underset{\|}{C}}\right)_c - O - (CR_7R_8)_o - (CR_9R_{10})_p \cdots$$

$$\cdots N\underset{}{\overset{R_{24}}{\underset{R_{25}}{\|}}}\overset{Y_1}{\underset{\|}{C}}-(Z)_d-A$$

wherein:

R$_1$ is selected from the group consisting of polyethylene glycol, and terminal branching groups;

Z and Z' are the same or different and are independently selected from the group consisting of hydrophobic moieties, bifunctional linking moieties, $$-L_5-\overset{Y_4}{\underset{\|}{C}}-$$

wherein L$_5$ is a bifunctional linker and Y$_4$ is O, S or NR$_{11}$, and combinations thereof;

Y$_{1-3}$ are the same or different and are selected from the group consisting of O, S and NR$_{11}$;

L$_1$ and L$_3$ are independently selected bifunctional linkers;

R$_3$-R$_{11}$, R$_{24}$ and R$_{25}$ are the same or different and are selected from the group consisting of hydrogen, C$_{1-6}$ alkyls, C$_{2-6}$ alkenyls, C$_{2-6}$ alkynyls, C$_{3-19}$ branched alkyls, C$_{3-8}$ cycloalkyls, C$_{1-6}$ substituted alkyls, C$_{2-6}$ substituted alkenyls, C$_{2-6}$ substituted alkynyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

L$_2$ is —C(O)(CR$_{30}$R$_{31}$)Y$_{15}$(CR$_{32}$R$_{33}$)C(O)NR$_{35}$— or —C(O)(CR$_{30}$R$_{31}$)(CR$_{32}$R$_{33}$)C(O)NR$_{35}$— wherein:

Y$_{15}$ is selected from the group consisting of O, S, NR$_{34}$ and CH$_2$; and R$_{30-35}$ are the same or different and are selected from the group consisting of H, alkyls, alkenyls, alkynyls, heteroalkyls and aryls;

A and A' may be the same or different and are independently selected from the group consisting of alkyl groups, leaving groups, functional groups, diagnostic agents, targeting moieties, biologically active moieties, and OH;

a, g, and e are the same or different and are independently 0 or a positive integer from 1 to 5;

b, c, d and d' are the same or different and are independently 0 or 1, and m, n, o, and p are the same or different and are independently a positive integer from 1 to 6, provided that (a+e) is equal to or greater than 1, wherein weight average molecular weight of polyethylene glycol is about 40,000 Da.

2. The compound of claim 1, wherein R$_3$-R$_{10}$, R$_{24-25}$ and R$_{30-34}$ are each hydrogen; and Y$_{15}$ is O or NR$_{34}$.

3. The compound of claim 1, wherein a, b, c, d, d', g, m, n, o and p are each 1.

4. The compound of claim 1, wherein A is a biologically active moiety, and A' is an alkyl group.

5. The compound of claim 1 wherein R$_1$ further comprises a capping group J, selected from the group consisting of OH, NH$_2$, SH, CO$_2$H, C$_{1-6}$ alkyl moieties, and $$A-(Z)_d-\overset{Y_1}{\underset{\|}{C}}\underset{R_{25}}{\overset{R_{24}}{\diagdown}}N\diagup\begin{matrix}(CR_5R_6)_m-(CR_3R_4)_n-O-(L_2)_e-(L_1)_a-\left(\overset{Y_2}{\underset{\|}{C}}\right)_b-\\(CR_9R_{10})_p-(CR_7R_8)_o-O-\left(\overset{Y_3}{\underset{\|}{C}}\right)_c-(L_3)_g-(Z')_{d'}-A'.\end{matrix}$$

6. A compound of claim 5, of the formula:

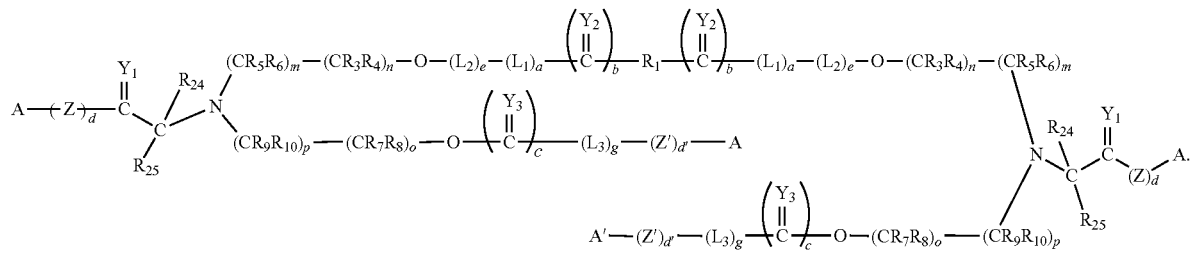

7. The compound of claim 1, wherein $R_1$ is selected from the group consisting of:

J-O-(CH₂CH₂O)$_x$-,

J-O-(CH₂CH₂O)$_x$-CH₂C(O)-O-,

J-O-(CH₂CH₂O)$_x$-CH₂CH₂NR₁₂-,

J-O-(C₂CH₂O)$_x$-CH₂CH₂S-,

-OC(O)CH₂-O-(CH₂CH₂O)$_x$-CH₂C(O)-O-,

-NR₁₂CH₂CH₂-O-(CH₂CH₂O)$_x$-CH₂CH₂NR₁₂- and

-SCH₂CH₂-O-(CH₂CH₂O)$_x$-CH₂CH₂S- wherein:
x is the degree of polymerization;
$R_{12}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and
J is a capping group.

8. The compound of claim 1, wherein $R_1$ is selected from the group consisting of:

CH₃-O-(CH₂CH₂O)$_x$-,

CH₃-O-(CH₂CH₂O)$_x$-CH₂C(O)-O-,

CH₃-O-(CH₂CH₂O)$_x$-CH₂CH₂NH- and

CH₃-O-(CH₂CH₂O)$_x$-CH₂CH₂S- wherein x is the degree of polymerization.

9. The compound of claim 1, wherein $R_1$ comprises a polymer residue of the formula -O-(CH₂CH₂O)$_x$- wherein:
x is the degree of polymerization.

10. The compound of claim 1 wherein $L_1$ and $L_3$ are independently selected from the group consisting of:

-NR₁₉(CR₁₄R₁₅)$_t$O-,

-NR₁₉(CR₁₄R₁₅)$_t$(CR₁₆CR₁₇O)$_s$NR₁₉-,

-O(CR₁₄R₁₅)$_t$NR₁₉-,

-O(CR₁₄R₁₅)$_t$O-,

-NR₁₉(CR₁₄R₁₅)$_t$NR₁₉-,

-NR₁₉(CR₁₄R₁₅)$_t$(CR₁₆CR₁₇O)$_s$-,

-NR₁₉(CR₁₆CR₁₇O)$_t$-,

-NR₁₉(CR₁₆CR₁₇O)$_t$(CR₁₄R₁₅)$_s$NR₁₉-,

-O(CR₁₆CR₁₇O)$_t$NR₁₉-,

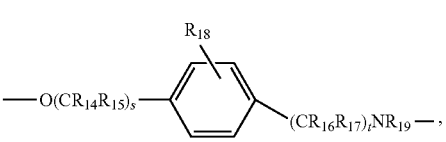

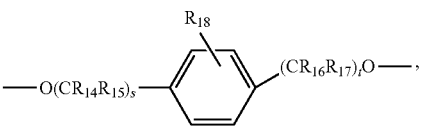

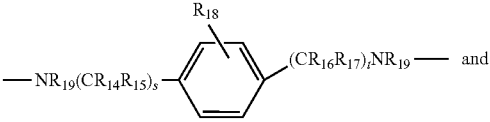

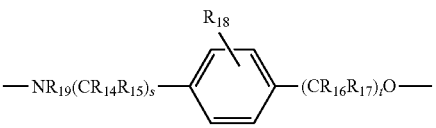

wherein:
$R_{14}$-$R_{17}$ and $R_{19}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$R_{18}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and t and s are individually selected positive integers from 1 to 4.

11. The compound of claim 1 wherein $L_2$ is selected from the group consisting of:

—C(O)CR$_{30}$R$_{31}$OCR$_{32}$R$_{33}$C(O)NR$_{35}$—,

—C(O)CR$_{30}$R$_{31}$NR$_{34}$CR$_{32}$R$_{33}$C(O)NR$_{35}$—,

—C(O)CR$_{30}$R$_{31}$SCR$_{32}$R$_{33}$C(O)NR$_{35}$— and

—C(O)(CR$_{30}$R$_{31}$)$_{n'}$C(O)NR$_{35}$— wherein:

$R_{30-34}$ are independently selected from the group consisting of H, $C_{1-6}$ alkyls, $C_{2-6}$ alkenyls, $C_{2-6}$ alkynyls, $C_{1-6}$ heteroalkyls and aryls; and n' is a positive integer from 1 to 3.

12. A compound of claim 1, wherein $R_1$ is selected from the group consisting of:

[structures]

wherein:

(q) is an integer of from 1 to 5;

Z" is O, NR$_{13}$, S, SO or SO$_2$ where $R_{13}$ is H, $C_{1-8}$ alkyl, $C_{1-8}$ branched alkyl, $C_{1-8}$ substituted alkyl, aryl or aralkyl;

(h) is 0 or 1; and (k) is a positive integer from 1 to 6.

13. A compound of claim 1, selected from the group consisting of:

(Ia)

(Ib)

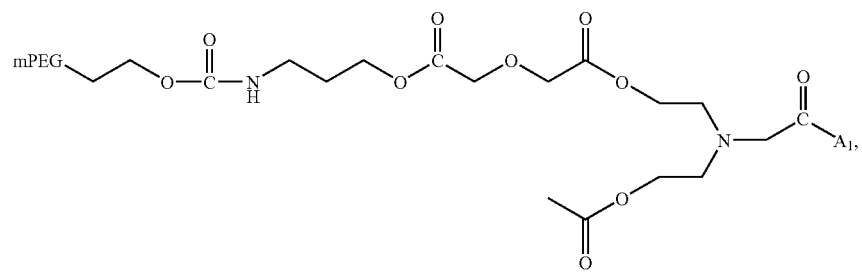
(Ic)
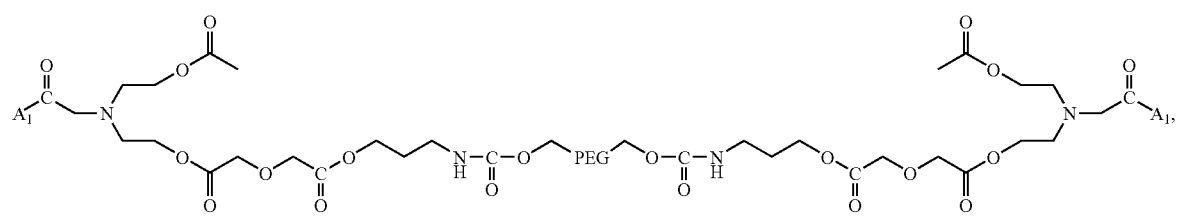
(Id)
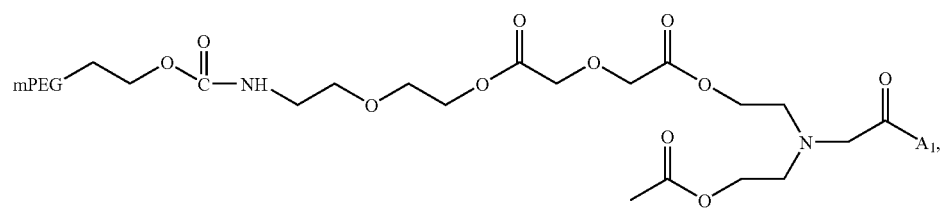
(Ie)
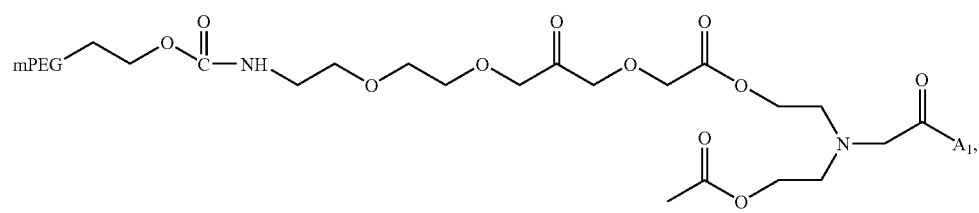
(If)
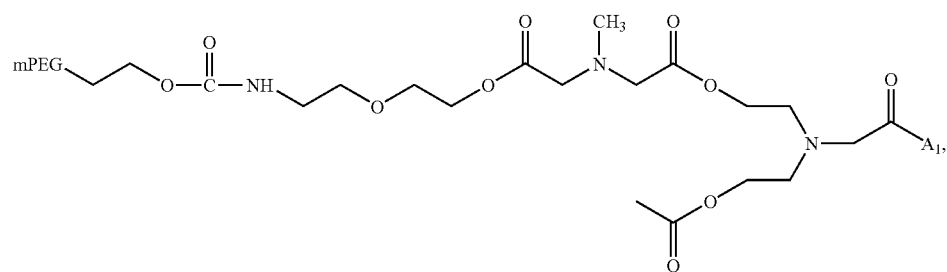
(Ig)

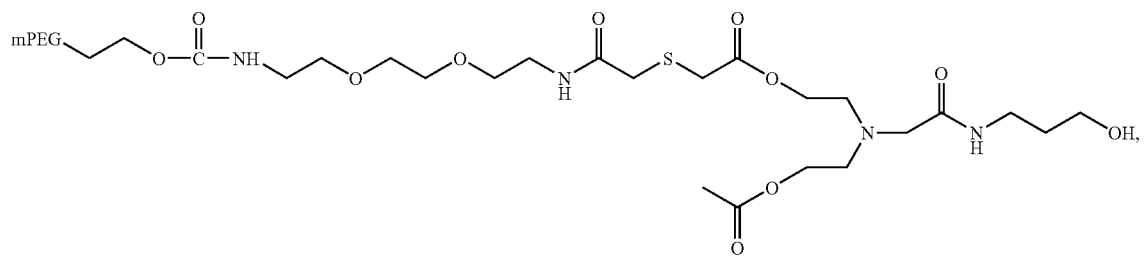
(Ih)
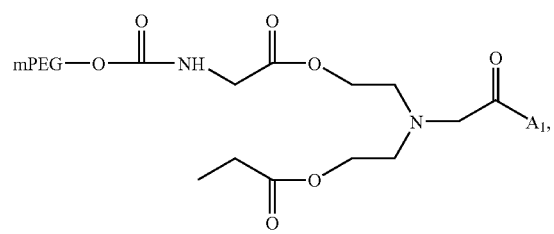
(Ii)
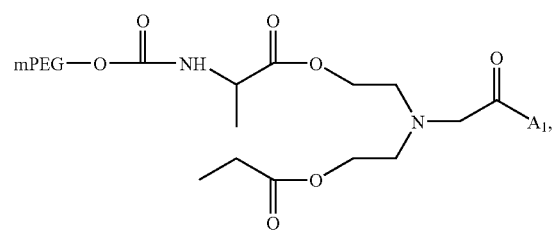
(Ij)
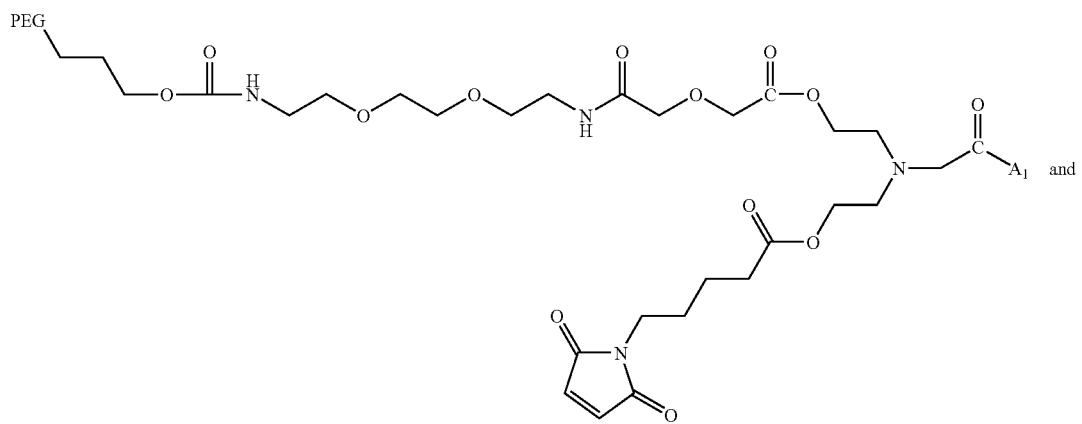
(Ik)
and
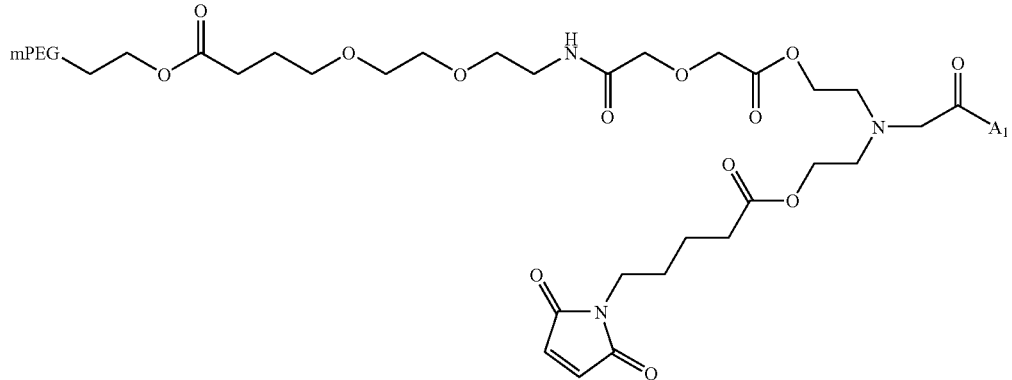
(Im)

wherein $A_1$ is a biologically active moiety selected from the group consisting of a residue of hydroxyl- or amine-containing organic compounds, peptides, and nucleic acids.

14. The compound of claim 1, wherein said terminal branching group comprises the formula:

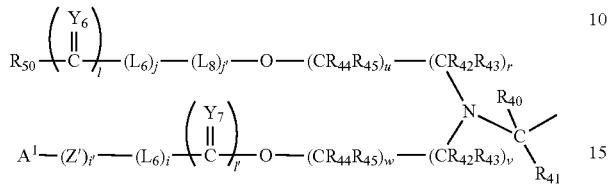

wherein:
$Y_6$ and $Y_7$ are independently O, S or $NR_{46}$;
$L_6$ is a bifunctional linker selected from the same group as that which defines $L_1$;
$L_8$ is a bifunctional linker selected from the same group as that which defines $L_2$;
$R_{40}$-$R_{46}$ are the same or different and are selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

j, j', i and i' are each independently 0 or a positive integer;
l and l' are independently 0 or 1;
u, r, v and w are independently selected positive integers; and
$R_{50}$ is selected from the group consisting of substantially non-antigenic polymer residues, and

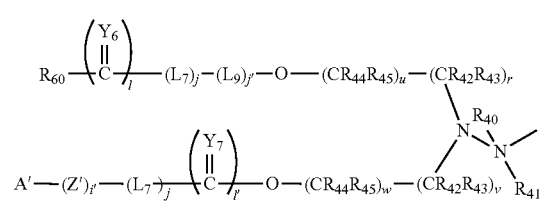

wherein:
$L_7$ is a bifunctional linker selected from the same group as that which defines $L_1$;
$L_9$ is a bifunctional linker selected from the same group as that which defines $L_2$; and
$R_{60}$ is polyethylene glycol.

15. A compound of claim 14, comprising the structure:

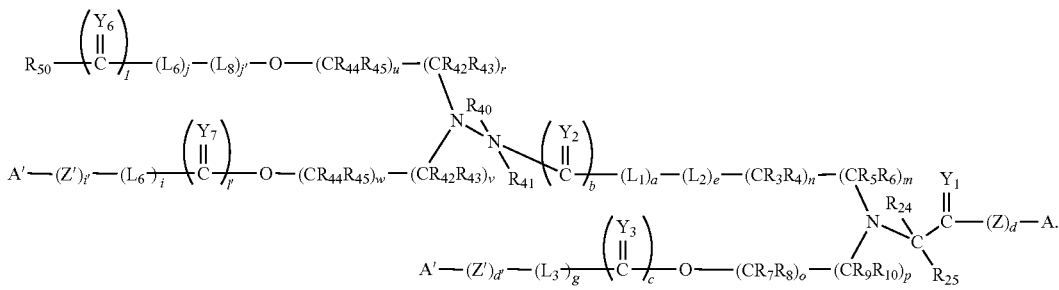

16. A compound of claim 15, comprising the structure:

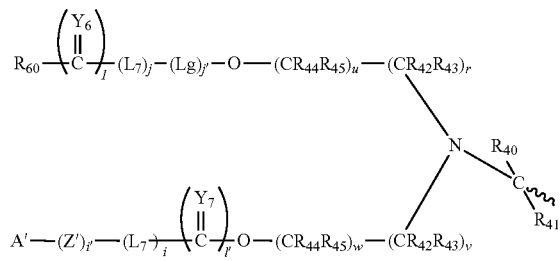

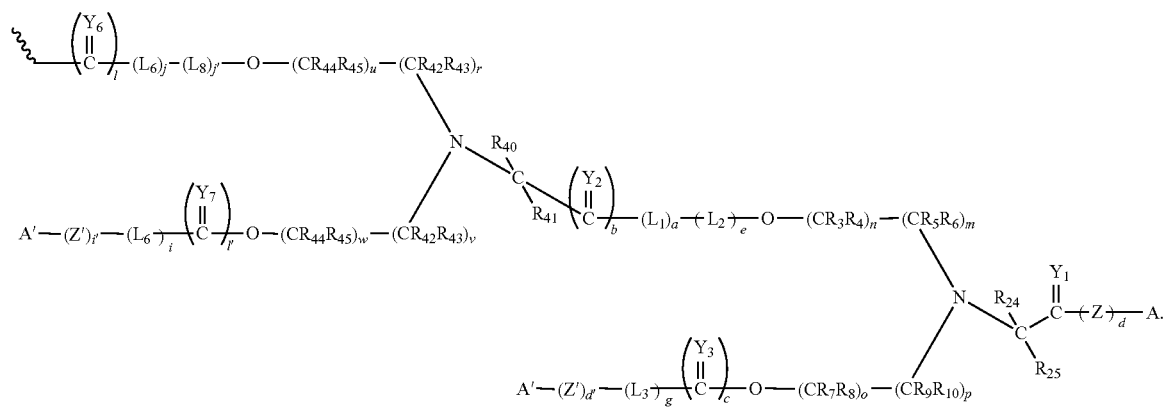
17. A compound of claim 1, selected from the group consisting of:
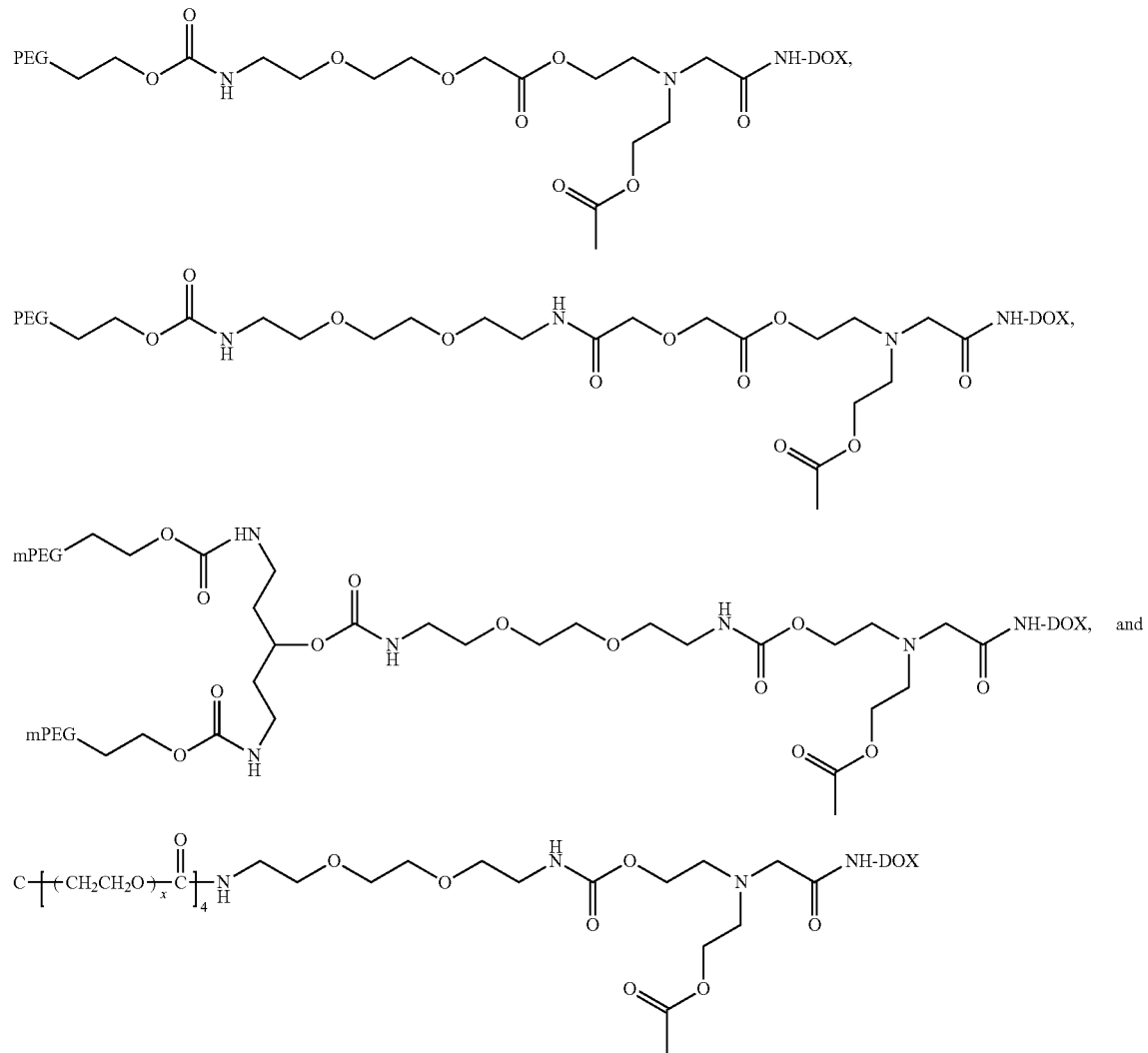

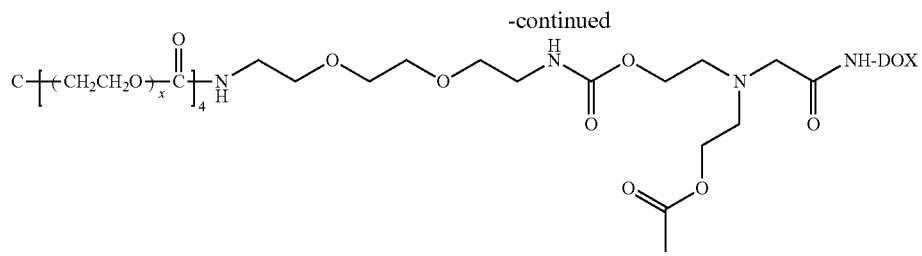
wherein:
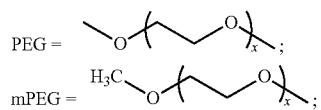
and
x is the degree of polymerization.
18. A compound of claim 1, selected from the group consisting of:
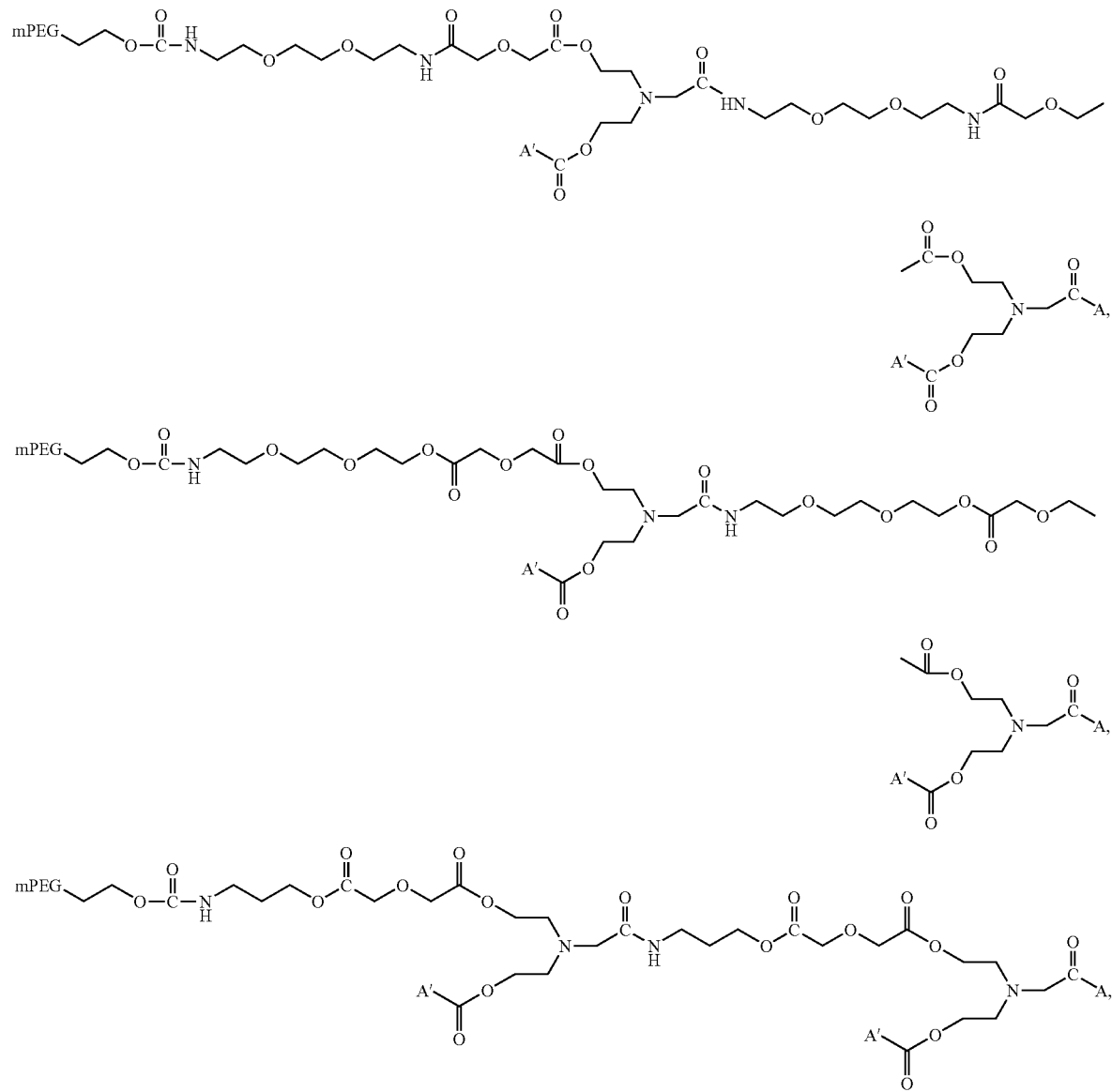

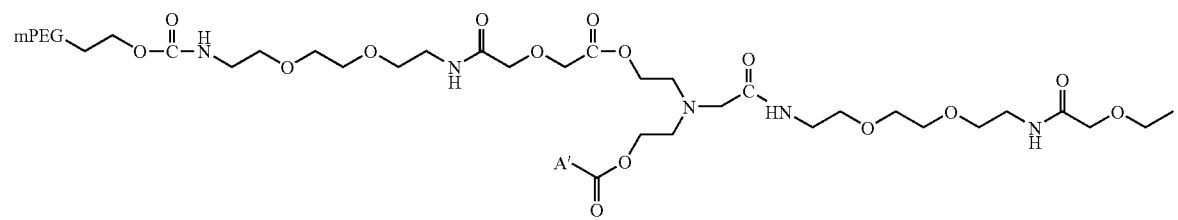
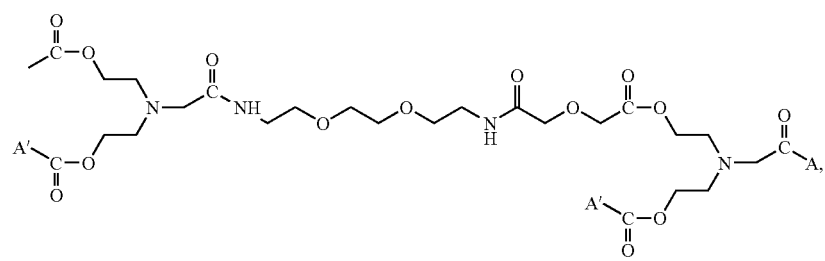
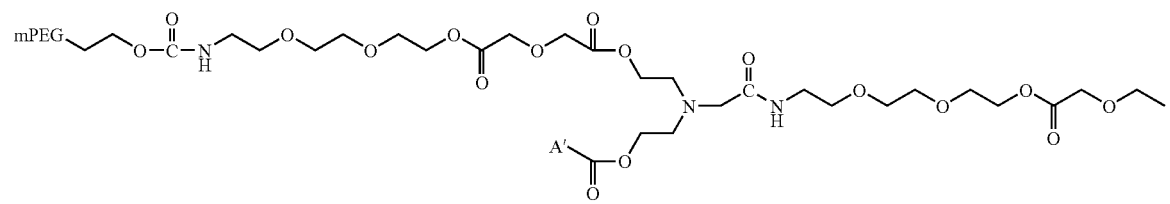
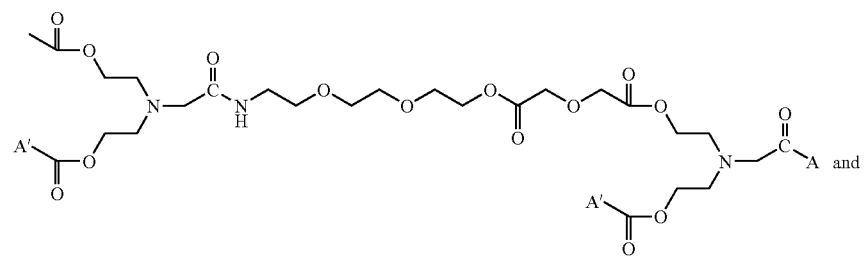
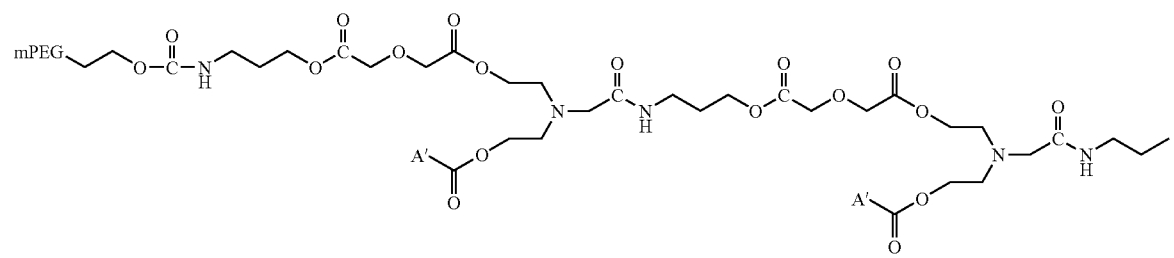

wherein
A is a biologically active moiety selected from the group consisting of a residue of hydroxyl- or amine-containing organic compounds;
A' is an alkyl group;

$$mPEG = \quad H_3C\text{—}O\text{—}(\text{—}O\text{—})_x\text{—};$$

and
x is the degree of polymerization.

19. A method of preparing a polymer conjugate, comprising reacting a compound of the formula:

$$R_1\text{—}(\overset{Y_2}{\underset{\|}{C}})_b\text{—}(L_1)_a\text{—}(L_2)_c\text{—}O\text{—}(CR_3R_4)_n\text{—}(CR_5R_6)_m\overset{R_{24}}{\underset{N}{\diagdown}}\overset{Y_1}{\underset{\|}{C}}\text{—}(Z)_d\text{—}A_1$$
$$A'\text{—}(Z')_{d'}\text{—}(L_3)_g\text{—}(\overset{Y_3}{\underset{\|}{C}})_c\text{—}O\text{—}(CR_7R_8)_o\text{—}(CR_9R_{10})_p\overset{}{\underset{R_{25}}{\diagup}}$$

wherein:
$A_1$ is a leaving group;
A' is selected from the group consisting of alkyl groups, leaving groups, functional groups, diagnostic agents, targeting moieties and OH;
$R_1$ is selected from the group consisting of polyethylene glycol, and terminal branching groups;
Z and Z' are the same or different and are independently selected from the group consisting of hydrophobic moieties, bifunctional linking moieties, $$\text{—}L_5\text{—}\overset{Y_4}{\underset{\|}{C}}\text{—}$$

wherein $L_5$ is a bifunctional linker and $Y_4$ is O, S or $NR_{11}$, and combinations thereof;

$Y_{1-3}$ are the same or different and are selected from the group consisting of O, S and $NR_{11}$;
$L_1$ and $L_3$ are independently selected bifunctional linkers;
$R_3$-$R_{11}$, $R_{24}$ and $R_{25}$ are the same or different and are selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$L_2$ is —C(O)(CR$_{30}$R$_{31}$)Y$_{15}$(CR$_{32}$R$_{33}$)C(O)NR$_{35}$— or —C(O)(CR$_{30}$R$_{31}$)(CR$_{32}$R$_{33}$)C(O)NR$_{35}$—
wherein:
$Y_{15}$ is selected from the group consisting of O, S, NR$_{34}$ and CH$_2$; and
$R_{30}$-$_{35}$ are the same or different and are selected from the group consisting of H, alkyls, alkenyls, alkynyls, heteroalkyls and aryls;
a, g, and e are the same or different and are independently 0 or a positive integer ranging from 1 to 5;
b, c, d and d' are independently 0 or 1; and
m, n, o, and p are independently positive integers ranging from 1 to 6;
provided that (a+e) is equal to or greater than 1;
with a biologically active agent under conditions sufficient to form a compound of Formula (I'):

$$R_1\text{—}(\overset{Y_2}{\underset{\|}{C}})_b\text{—}(L_1)_a\text{—}(L_2)_e\text{—}O\text{—}(CR_3R_4)_n\text{—}(CR_5R_6)_m\overset{R_{24}}{\underset{N}{\diagdown}}\overset{Y_1}{\underset{\|}{C}}\text{—}(Z)_d\text{—}A_2$$
$$A'\text{—}(Z')_{d'}\text{—}(L_3)_g\text{—}(\overset{Y_3}{\underset{\|}{C}})_c\text{—}O\text{—}(CR_7R_8)_o\text{—}(CR_9R_{10})_p\overset{}{\underset{R_{25}}{\diagup}}$$
(I')

wherein $A_2$ is a residue of a biologically active agent selected from the group consisting of organic compounds, peptides and nucleic acids, and wherein weight average molecular weight of the polyethylene glycol of Formula (I') is about 40,000 Da.

20. A method of treatment, comprising administering to a mammal in need thereof, an effective amount of a compound of claim 1, wherein A' is an alkyl group and A is a residue of a biologically active moiety selected from the group consisting of a residue of hydroxyl- or amine-containing organic compounds, peptides and nucleic acids.

21. The compound of claim 1, wherein a, b, c, d, m, n, o and p are each 1.

22. The compound of claim 1, wherein A' is an alkyl group and A is a residue of a biologically active moiety selected from the group consisting of a residue of hydroxyl- or amine-containing organic compounds, peptides and nucleic acids.

23. The compound of claim 1, wherein d' and g are 0.

* * * * *

UNITED STATES PATENT AND TRADEMARK OFFICE
CERTIFICATE OF CORRECTION

PATENT NO. : 8,192,743 B2
APPLICATION NO. : 12/180187
DATED : June 5, 2012
INVENTOR(S) : Hong Zhao et al.

It is certified that error appears in the above-identified patent and that said Letters Patent is hereby corrected as shown below:

a) <u>Column 44, in claim 12</u>, second formula

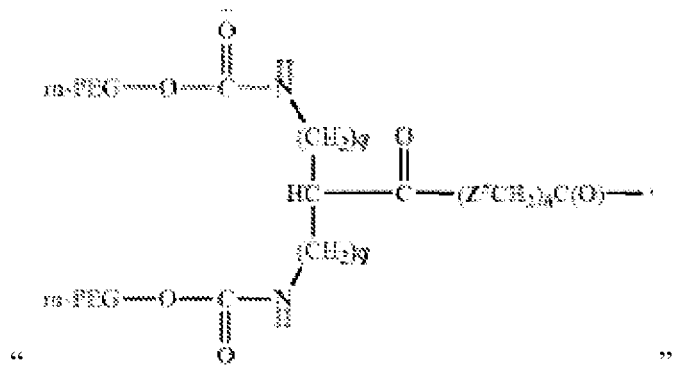

should be

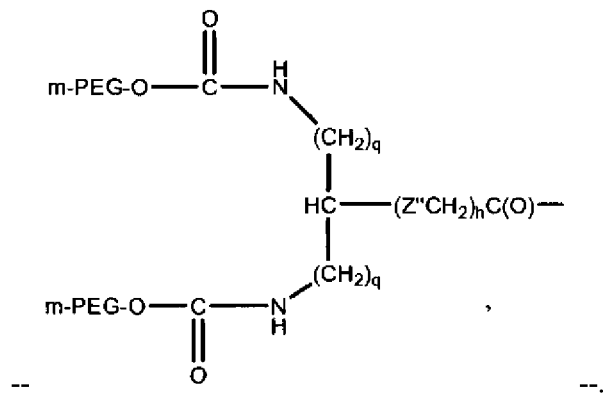

Signed and Sealed this
Twenty-fifth Day of September, 2012

David J. Kappos
*Director of the United States Patent and Trademark Office*

CERTIFICATE OF CORRECTION (continued)
U.S. Pat. No. 8,192,743 B2 b) Column 49, in claim 16, the formula

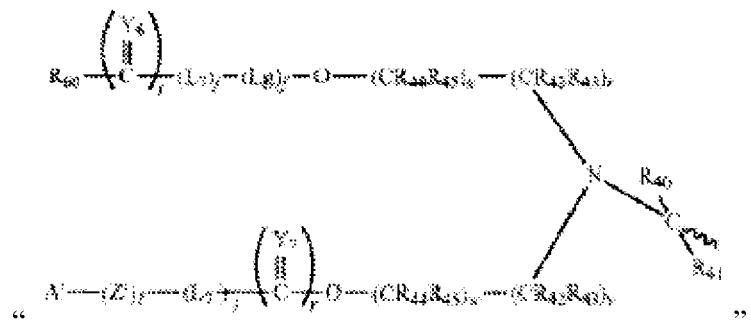

should be

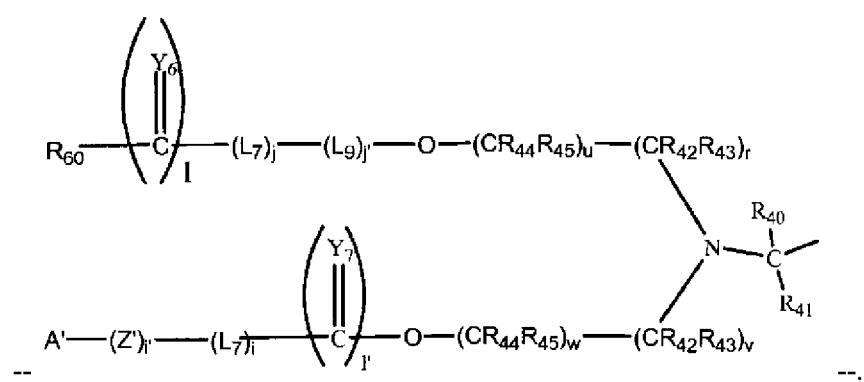

c) Column 50, in claim 14, second formula

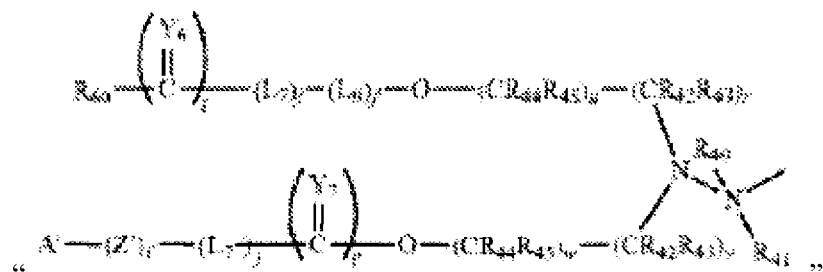

should be

CERTIFICATE OF CORRECTION (continued)
U.S. Pat. No. 8,192,743 B2

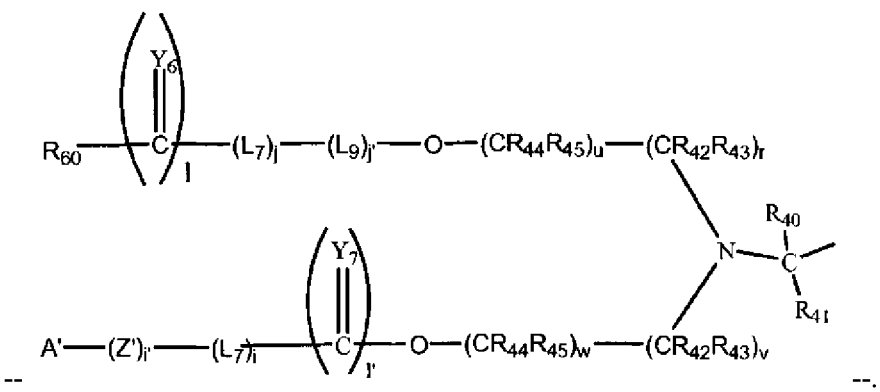

d) <u>Columns 53-54, in claim 17</u>, the top formula

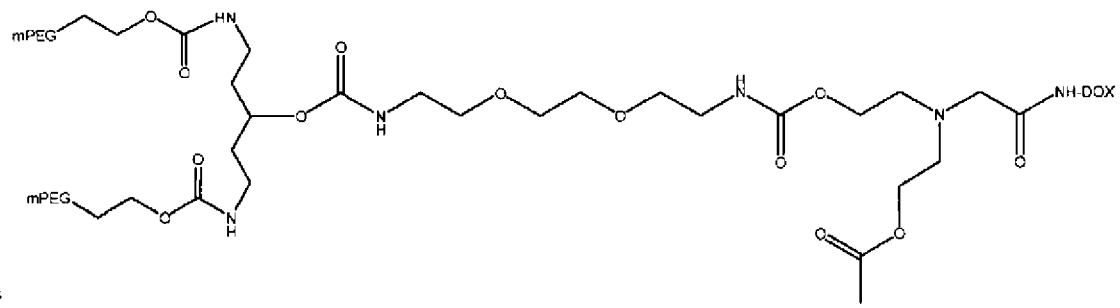

" "

is a duplicate and should be deleted.

e) <u>Column 57, in claim 19</u>, the formula

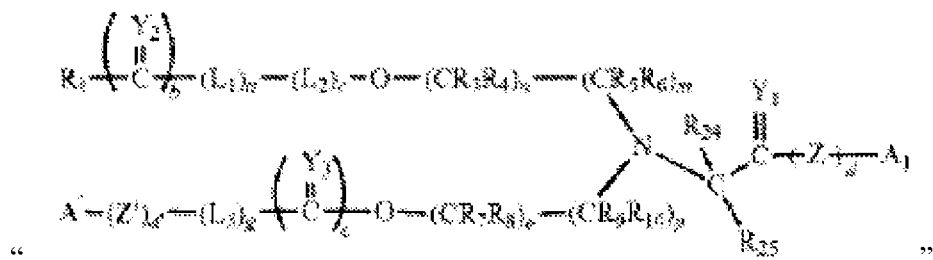

" "

should be

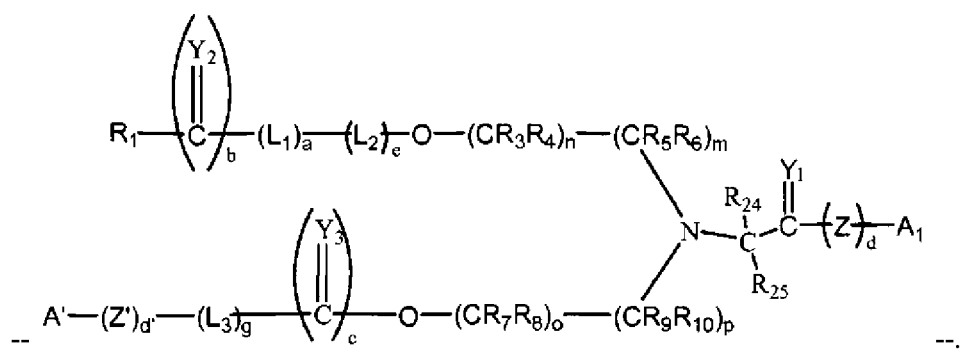

CERTIFICATE OF CORRECTION (continued)
U.S. Pat. No. 8,192,743 B2 f) <u>Column 58, in claim 19</u>, second formula

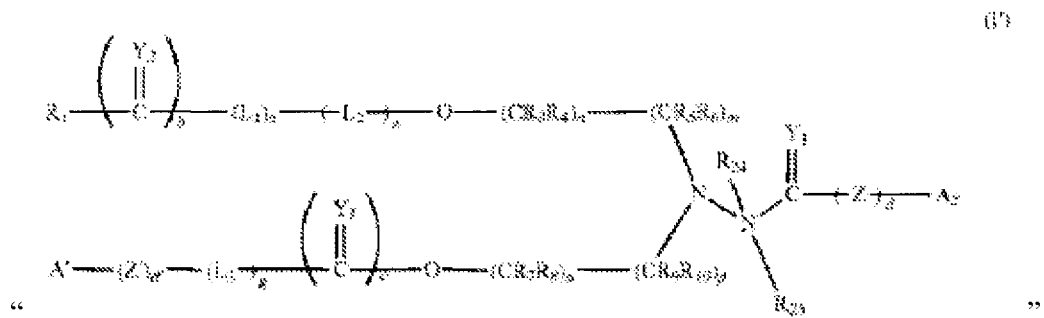

should be